(12) United States Patent
Fuls et al.

(10) Patent No.: US 8,337,872 B2
(45) Date of Patent: *Dec. 25, 2012

(54) METHOD OF INHIBITING THE TRANSMISSION OF INFLUENZA VIRUS

(75) Inventors: Janice L. Fuls, Fountain Hills, AZ (US); Nancy D. Rodgers, Chandler, AZ (US); Richard F. Theiler, Scottsdale, AZ (US); Daniel E. Pedersen, Cottage Grove, MN (US); John J. Rolando, Woobury, MN (US); Richard K. Staub, Lakeville, MN (US)

(73) Assignee: The Dial Corporation, Scottsdale, AZ (US)

( * ) Notice: Subject to any disclaimer, the term of this patent is extended or adjusted under 35 U.S.C. 154(b) by 949 days.

This patent is subject to a terminal disclaimer.

(21) Appl. No.: 11/809,068

(22) Filed: May 31, 2007

(65) Prior Publication Data

US 2007/0280901 A1    Dec. 6, 2007

Related U.S. Application Data

(60) Provisional application No. 60/810,389, filed on Jun. 2, 2006, provisional application No. 60/811,354, filed on Jun. 6, 2006.

(51) Int. Cl.
| | | |
|---|---|---|
| A01N 25/00 | (2006.01) | |
| A01N 37/00 | (2006.01) | |
| A61K 8/02 | (2006.01) | |
| A61K 31/765 | (2006.01) | |
| A61K 31/19 | (2006.01) | |

(52) U.S. Cl. .............. 424/405; 424/401; 424/78.37; 514/557; 514/574

(58) Field of Classification Search .................. None
See application file for complete search history.

(56) References Cited

U.S. PATENT DOCUMENTS

| | | |
|---|---|---|
| 3,393,155 A | 7/1968 | Schutte |
| 3,929,678 A | 12/1975 | Laughlin et al. |
| 4,503,070 A | 3/1985 | Eby, III |
| 4,647,458 A | 3/1987 | Ueno et al. |
| 4,767,788 A | 8/1988 | Diana |
| 4,942,029 A * | 7/1990 | Scheps ................. 424/78.07 |
| 4,970,216 A | 11/1990 | Deckner et al. |
| 4,975,217 A | 12/1990 | Brown-Skrobot et al. |
| 5,017,617 A | 5/1991 | Kihara et al. |
| 5,043,357 A | 8/1991 | Hoffler et al. |
| 5,049,440 A | 9/1991 | Bornhoeft, III et al. |
| 5,070,126 A | 12/1991 | Toyonishi et al. |
| 5,200,189 A | 4/1993 | Oakes et al. |
| 5,314,687 A | 5/1994 | Oakes et al. |
| 5,316,688 A | 5/1994 | Gladfelter et al. |
| 5,389,390 A | 2/1995 | Kross |
| 5,403,864 A | 4/1995 | Bruch et al. |
| 5,409,713 A | 4/1995 | Lokkesmoe et al. |
| 5,409,905 A | 4/1995 | Eby, III |
| 5,439,681 A | 8/1995 | Khan et al. |
| 5,622,724 A | 4/1997 | Bryce-Smith |
| 5,629,006 A | 5/1997 | Hoang et al. |
| 5,635,462 A | 6/1997 | Fendler et al. |
| 5,639,795 A | 6/1997 | Friedman et al. |
| 5,714,374 A | 2/1998 | Arnold et al. |
| 5,718,910 A | 2/1998 | Oakes et al. |
| 5,728,404 A | 3/1998 | von Rheinbaben et al. |
| 5,776,430 A | 7/1998 | Osborne et al. |
| 5,798,329 A | 8/1998 | Taylor et al. |
| 5,800,827 A | 9/1998 | Igarashi et al. |
| 5,830,487 A | 11/1998 | Klofta et al. |
| 5,929,016 A | 7/1999 | Harrison |
| 5,942,478 A | 8/1999 | Lopes |
| 5,968,539 A | 10/1999 | Beerse et al. |
| 6,022,551 A | 2/2000 | Jampani et al. |
| 6,034,133 A | 3/2000 | Hendley et al. |
| 6,063,425 A | 5/2000 | Kross et al. |
| 6,080,417 A | 6/2000 | Kramer et al. |
| 6,090,772 A | 7/2000 | Kaiser et al. |
| 6,106,851 A | 8/2000 | Beerse et al. |
| 6,107,261 A | 8/2000 | Taylor et al. |
| 6,110,908 A | 8/2000 | Guthery |
| 6,113,933 A | 9/2000 | Beerse et al. |
| 6,113,963 A | 9/2000 | Gutzmann et al. |
| 6,136,771 A | 10/2000 | Taylor et al. |
| 6,183,807 B1 | 2/2001 | Gutzmann et al. |

(Continued)

FOREIGN PATENT DOCUMENTS

DE    2822608    11/1979

(Continued)

OTHER PUBLICATIONS

Bieker et al., "Inactivation of Various Influenza Strains to Model Avian Influenz (Bird Flu) With Various Disinfectant Chemistries," Sandia Report, printed Dec. 2005.*
Haley et al, Bactericidal Activity of Antiseptics Against Methicillin-Resistant *Staphylococcus aureus*, Journal of Clinical Microbiology, vol. 21, No. 6, 1985, p. 991-992.
McKeough et al, Comparison of New Topical Treatments for Herpes Labialis, Arch Dermatol, 2001, vol. 137, p. 1153-1158.
Poli et al, Virucidal Activity of Organic Acids, Food Chemistry, vol. 4, No. 4, p. 251-258 (1979).
International Search Report for international application No. PCT/US2007/012321, dated Jul. 3, 2008.
International Search Report for international application No. PCT/US2007/012331, dated Jul. 2, 2008.

(Continued)

*Primary Examiner* — Sreeni Padmanabhan
*Assistant Examiner* — Jody Karol
(74) *Attorney, Agent, or Firm* — Marshall, Gerstein & Borun LLP

(57) ABSTRACT

Antimicrobial compositions having a rapid and persistent antiviral effectiveness against influenza viruses, including avian flu viruses, are disclosed. The antimicrobial compositions contain (a) a disinfecting alcohol, (b) an organic acid, and (c) water, wherein the composition has a pH of about 5 or less and the nonvolatile components of the composition are capable of forming a barrier film or layer on a treated surface.

34 Claims, 1 Drawing Sheet

U.S. PATENT DOCUMENTS

| | | |
|---|---|---|
| 6,190,674 B1 | 2/2001 | Beerse et al. |
| 6,190,675 B1 | 2/2001 | Beerse et al. |
| 6,204,230 B1 | 3/2001 | Taylor et al. |
| 6,210,695 B1 | 4/2001 | Beerse et al. |
| 6,214,363 B1 | 4/2001 | Beerse et al. |
| 6,217,887 B1 | 4/2001 | Beerse et al. |
| 6,248,343 B1 | 6/2001 | Jampani et al. |
| 6,294,186 B1 | 9/2001 | Beerse et al. |
| 6,358,906 B1 | 3/2002 | Ochs et al. |
| 6,376,437 B2 | 4/2002 | Viscovitz et al. |
| 6,432,906 B1 | 8/2002 | Carlson et al. |
| 6,436,885 B2 | 8/2002 | Biedermann et al. |
| 6,451,748 B1 | 9/2002 | Taylor et al. |
| 6,475,501 B1 | 11/2002 | Kelly et al. |
| 6,488,942 B1 | 12/2002 | Ingemann et al. |
| 6,514,556 B2 | 2/2003 | Hilgren et al. |
| 6,517,849 B1 | 2/2003 | Seger et al. |
| 6,545,047 B2 | 4/2003 | Gutzmann et al. |
| 6,551,553 B1 | 4/2003 | von Rheinbaben et al. |
| 6,559,110 B1 | 5/2003 | Lopes |
| 6,608,121 B2 | 8/2003 | Isozaki et al. |
| 6,610,314 B2 | 8/2003 | Koenig et al. |
| 6,632,291 B2 | 10/2003 | Rabon et al. |
| 6,657,004 B2 | 12/2003 | Mizutani |
| 6,673,835 B1 | 1/2004 | Hensley et al. |
| 6,787,512 B1 | 9/2004 | Verrall et al. |
| 6,855,341 B2 | 2/2005 | Smith |
| 6,858,232 B2 | 2/2005 | Verbiscar |
| 6,921,529 B2 | 7/2005 | Maley |
| 6,956,070 B2 | 10/2005 | Fujiwara et al. |
| 7,005,451 B1 | 2/2006 | Nevermann et al. |
| 7,208,453 B2 | 4/2007 | Nevermann et al. |
| 7,268,163 B2 | 9/2007 | Konowalchuk et al. |
| 7,592,300 B2 | 9/2009 | Taylor et al. |
| 2001/0053378 A1 | 12/2001 | Chilakos |
| 2002/0098159 A1 | 7/2002 | Wei et al. |
| 2002/0161046 A1 | 10/2002 | Konowalchuk et al. |
| 2002/0165277 A1 | 11/2002 | Konowalchuk et al. |
| 2002/0165279 A1 | 11/2002 | Konowalchuk et al. |
| 2002/0182348 A1 | 12/2002 | Fujiwara et al. |
| 2003/0175323 A1 | 9/2003 | Utterberg et al. |
| 2003/0235550 A1 | 12/2003 | Pan et al. |
| 2004/0001797 A1 | 1/2004 | Saud et al. |
| 2004/0086575 A1 | 5/2004 | Smith |
| 2004/0096521 A1 | 5/2004 | Clawson |
| 2004/0214785 A1 | 10/2004 | Dees et al. |
| 2004/0234457 A1 | 11/2004 | Rennie et al. |
| 2005/0013836 A1 | 1/2005 | Raad |
| 2005/0042240 A1 | 2/2005 | Utterberg et al. |
| 2005/0159321 A1 | 7/2005 | Cusack et al. |
| 2005/0203187 A1 | 9/2005 | Verbiscar |
| 2005/0232868 A1 | 10/2005 | Rennie et al. |
| 2005/0232895 A1 | 10/2005 | Chen |
| 2005/0238728 A1 | 10/2005 | Evans |
| 2005/0271711 A1 | 12/2005 | Lynch et al. |

FOREIGN PATENT DOCUMENTS

| | | |
|---|---|---|
| EP | 0259249 | 3/1988 |
| EP | 0208403 B1 | 1/1990 |
| EP | 0375827 | 7/1990 |
| EP | 0394928 A1 | 10/1990 |
| EP | 0444230 | 9/1991 |
| EP | 0505935 | 9/1992 |
| EP | 0604848 | 7/1994 |
| EP | 0651048 | 5/1995 |
| EP | 0707794 | 4/1996 |
| EP | 0251303 | 1/1998 |
| EP | 0937394 | 8/1999 |
| EP | 1158016 | 11/2001 |
| EP | 1180536 | 2/2002 |
| EP | 1251147 | 10/2002 |
| FR | 1568905 A | 5/1969 |
| GB | 933684 | 8/1963 |
| GB | 1126953 | 9/1968 |
| GB | 2187097 A | 9/1987 |
| GB | 2 231 496 | 11/1990 |
| GB | 2391810 | 2/2004 |
| JP | 07252105 A | 10/1995 |
| JP | 10087410 A | 4/1998 |
| SE | 466111 | 12/1991 |
| WO | WO-91/19222 | 12/1991 |
| WO | WO-93/07250 | 4/1993 |
| WO | WO-93/16597 | 9/1993 |
| WO | WO-95/09605 | 4/1995 |
| WO | WO-95/32705 | 12/1995 |
| WO | WO-96/06152 | 2/1996 |
| WO | WO96/11572 A1 | 4/1996 |
| WO | WO96/24247 A1 | 8/1996 |
| WO | WO-96/29867 | 10/1996 |
| WO | WO-97/15647 | 5/1997 |
| WO | WO-97/46218 | 12/1997 |
| WO | WO-98/01110 | 1/1998 |
| WO | WO-98/44792 | 10/1998 |
| WO | WO98/44794 A1 | 10/1998 |
| WO | WO-98/55096 | 12/1998 |
| WO | WO99/20228 | 4/1999 |
| WO | WO00/27192 A1 | 5/2000 |
| WO | WO-00/43047 | 7/2000 |
| WO | WO-00/78141 | 12/2000 |
| WO | WO-00/78275 | 12/2000 |
| WO | WO-01/28337 | 4/2001 |
| WO | WO-01/28338 | 4/2001 |
| WO | WO-01/28339 | 4/2001 |
| WO | WO-01/28340 | 4/2001 |
| WO | WO01/41567 A1 | 6/2001 |
| WO | WO01/41573 A1 | 6/2001 |
| WO | WO-01/79417 | 10/2001 |
| WO | WO02/059244 A2 | 8/2002 |
| WO | WO-02/069887 | 9/2002 |
| WO | WO02/078667 A1 | 10/2002 |
| WO | WO-2004/000016 | 12/2003 |
| WO | WO-2004/004677 | 1/2004 |
| WO | WO-2004/016087 | 2/2004 |
| WO | WO-2004/021786 | 3/2004 |
| WO | WO-2004/080179 | 9/2004 |
| WO | WO-2004/086575 | 10/2004 |
| WO | WO-2005/067878 | 7/2005 |
| WO | WO-2005/074947 | 8/2005 |
| WO | WO2006/062857 A2 | 6/2006 |
| WO | WO2007/095008 A2 | 8/2007 |
| ZA | 200308879 | 5/2004 |

OTHER PUBLICATIONS

International Search Report for international application No. PCT/US2007/012647, dated Aug. 4, 2008.

International Search Report for international application No. PCT/US2007/012735, dated Jul. 2, 2008.

International Search Report for international application No. PCT/US2007/012318, dated Jul. 2, 2008.

International Search Report for international application No. PCT/US2007/013136, dated Jul. 2, 2008.

Database WPI Week 199202 Derwent Publications Ltd., London, GB; AN 1989-136366 XP002429055 & SE 466111B (ASTRA AB) Dec. 16, 1991.

Malik et al, Comparative Efficacy of Ethanol and Isopropanol Against Feline Calicivirus, a Norovirus Surrogate, Amer. Jour. of Infec. Cont., 34(1):31-35 (2006).

Allawala et al., "The release of antimicrobial agents from solutions of surface-active agents," J. Am. Pharm. Assoc., 42:267-275 (1953).

Hayden et al., "Inactivation of rhinovirus on human fingers by virucidal activity of glutaric acid," Antimicrob. Agents Chemother., 26:928-929 (1984).

Hayden et al., "The effect of placebo and virucidal paper handkerchiefs on viral contamination of the hand and transmission of experimental rhinoviral infection," J. Infect. Dis., 152:403-407 (1985).

International Search Report for international application No. PCT/US2005/043720, dated Oct. 6, 2006.

International Search Report fo nternational application No. PCT/US2005/043765, dated Sep. 28, 2006.

International Search Report for international application No. PCT/US2005/043766, dated Oct. 12, 2006.

International Search Report for international application No. PCT/US2005/043767, dated Oct. 4, 2006.

International Search Report for international application No. PCT/US2005/043794, dated Sep. 28, 2006.
International Search Report for international application No. PCT/US2005/043910, dated Apr. 12, 2007.
International Search Report for international application No. PCT/US2005/043921, dated Oct. 17, 2006.
Mitchell, "Bactericidal activity of chloroxylenol in aqueous solutions of cetomacrogol," *J. Pharmacol.*, 16:533-537 (1964).
Sattar et al., "Chemical disinfection to interrupt transfer of rhinovirus type 14 from environmental surfaces to hands," *Appl. Environ. Microbiol.*, 59:1579-1585 (1993).
Written Opinion of the International Searching Authority for international application No. PCT/US2005/043921, dated Oct. 17, 2006.
Written Opinion of the International Searching Authority for the international application No. PCT/US2005/043720, dated Jun. 21, 2007.
Written Opinion of the International Searching Authority for international application No. PCT/US2005/043765, dated Sep. 28, 2006.
Written Opinion of the International Searching Authority for international application No. PCT/US2005/043766, dated Oct. 12, 2006.
Written Opinion of the International Searching Authority for international application No. PCT/US2005/043767, dated Oct. 4, 2006.
Written Opinion of the International Searching Authority for international application No. PCT/US2005/043794, dated Sep. 28, 2006.
Written Opinion of the International Searching Authority for international application No. PCT/US2005/043910, dated Apr. 12, 2007.
Kramer et al., "Virucidal Activity of a New Hand Disinfectant with Reduced Ethanol Content: Comparison with Other Alcohol-Based Formulations," *Journal of Hospital Infection*, 62, 98-106 (2006).
International Search Report in PCT/US2007/012794, filed Jul. 1, 2008.

* cited by examiner

METHOD OF INHIBITING THE TRANSMISSION OF INFLUENZA VIRUS

CROSS-REFERENCE TO RELATED APPLICATIONS

This application claims the benefit of U.S. Provisional Patent Application No. 60/810,389, filed Jun. 2, 2006 and U.S. Provisional Patent Application No. 60/811,354, filed Jun. 6, 2006.

FIELD OF THE INVENTION

The present invention relates to antimicrobial compositions capable of inhibiting the transmission of an influenza virus, and in particular an avian flu virus. More particularly, the present invention relates to antimicrobial compositions comprising (a) a disinfecting alcohol and (b) an organic acid. The combination of (a) and (b) can synergistically inactivate or destroy influenza viruses, such as the H5N1 avian flu virus, based on the log P (water-octanol partition coefficient) of the organic acid. The compositions provide a substantial reduction in influenza virus populations within one minute. In some embodiments, compositions provide a barrier layer, or film, comprising the organic acid on a treated surface to impart a persistent antiviral activity to the surface.

BACKGROUND OF THE INVENTION

Human health is impacted by a variety of microbes encountered on a daily basis. In particular, contact with various microbes in the environment can lead to an illness, possibly severe or lethal, in mammals. For example, microbial contamination can lead to a variety of illnesses, including, but not limited to, food poisoning, a streptococcal infection, anthrax (cutaneous), influenza, athlete's foot, cold sores, conjunctivitis ("pink eye"), coxsackievirus (hand-foot-mouth disease), croup, diphtheria (cutaneous), ebolic hemorrhagic fever, and impetigo.

Viruses are a category of pathogens of primary concern. Viral infections are among the greatest causes of human morbidity, with an estimated 60% or more of all episodes of human illness in developed countries resulting from a viral infection. In addition, viruses infect virtually every organism in nature, with high virus infection rates occurring among birds, including fowl and migrating birds, and mammals, including humans, pets, livestock, and zoo specimens.

Viruses exhibit an extensive diversity in structure and life cycle. A detailed description of virus families, their structures, life cycles, and modes of viral infection is discussed in *Fundamental Virology*, 4th Ed., Eds. Knipe & Howley, Lippincott Williams & Wilkins, Philadelphia, Pa., 2001.

Simply stated, virus particles are intrinsic obligate parasites, and have evolved to transfer genetic material between cells and encode sufficient information to ensure their propagation. In a most basic form, a virus consists of a small segment of nucleic acid encased in a simple protein shell. The broadest distinction between viruses is the enveloped and nonenveloped viruses, i.e., those that do or do not contain, respectively, a lipid-bilayer membrane.

Viruses propagate only within living cells. The principal obstacle encountered by a virus is gaining entry into the cell, which is protected by a cell membrane of thickness comparable to the size of the virus. In order to penetrate a cell, a virus first must become attached to the cell surface. Much of the specificity of a virus for a certain type of cell lies in its ability to attach to the surface of that specific cell. Durable contact is important for the virus to infect the host cell, and the ability of the virus and the cell surface to interact is a property of both the virus and the host cell. The fusion of viral and host-cell membranes allows the intact viral particle, or, in certain cases, only its infectious nucleic acid to enter the cell. Therefore, in order to control a viral infection, it is important to rapidly kill a virus that contacts the skin, and ideally to provide a persistent antiviral activity on the skin, or a hard surface, in order to control viral infections.

Influenza viruses belong to the family Orthomyxovirdae. They are enveloped viruses, and the family contains five genera classified by variations in nucleoprotein antigens. The five genera are influenza A, influenza B, influenza C, thogotovirus, and isavirus.

Influenza virus A consists of a single species. Influenza A viruses are the major cause of influenza in humans, and all past pandemics have been caused by influenza A viruses. The influenza A genome consists of 10 genes encoding for different proteins. The two surface proteins are glycoproteins, i.e., hemagglutinin (HA) and neuraminidase (NA). These proteins are distributed evenly over the virion surface. It is the antigenic variation in these proteins that is used to define the subtypes of influenza A.

There are 16 different HA antigens (H1-H16) and nine different NA antigens (N1-N9). Human disease has historically been caused by three subtypes of HA, i.e., H1, H2, and H3, and two subtypes of NA, i.e., N1 and N2. Recently it has been recognized that human disease can be caused by other HA antigens (e.g., H5, H7, and H9).

All known subtypes of influenza A can be found in birds, and feral aquatic birds are the major reservoir for influenza A. Typically, the disease does not affect feral birds, but domestic chickens and turkeys are susceptible to severe and fatal influenza. Other mammals are also susceptible to influenza, and influenza A has caused disease in horses, pigs, whales, and seals. Furthermore, the range of subtypes that cause disease in additional species (e.g., cats, civets, dogs) is expanding.

Avian influenza is the term used to describe influenza A subtypes that primarily affect chickens, turkeys, guinea fowl, migratory fowl, and other avian species. Avian strains also are classified according to their disease severity. Two recognized forms are highly pathogenic avian influenza (HPAI) and low pathogenic avian influenza (LPAI). HPAI strains typically result in mortality rates of 100% in flocks. The current H5N1 strain is an HPAI, however, there are other strains of H5N1 that are LPAI. Human infections have been associated with both HPAI and LPAI.

The virus strain responsible for the 1918 pandemic flu was an H1N1. This strain has been reconstructed and appears to be of avian origin. The pandemic strains of 1957-58 (H2N2) and 1968-69 (H3N2) both involved reassortment between avian and human strains. Influenza nomenclature is based on (a) host of origin (if other than human), (b) geographic origin, (c) strain number, (d) year of isolation, and (e) HA and NA type. Some examples would be: A/Hong Kong/03/68(H3N2), or A/swine/iowa/15/30(H1N1). Structurally, all influenza types are the same, and for this reason a composition and method of that can inactivate or destroy one type of influenza, also can inactivate or destroy other types of influenza regardless of the genus, subtype, or species in which they infect.

Recently, avian influenza viruses emerged as a pandemic threat to the health of humans. The threat that most concerns scientists and health authorities is the deadly H5N1 avian flu virus. The H5N1 avian flu virus has ravaged poultry stocks in Asia since 2003 and recently has spread to Europe through migratory birds. More than 160 people have died of the avian flu since 2003. However, human cases of the disease have been limited to individuals who came into direct contact with infected birds. Health authorities fear this disease will mutate into a form that spreads easily from person-to-person, which can initiate a flu pandemic that could kill millions of people. It is feared that death tolls could be on the level of the 1918-1919 Spanish flu pandemic, which is estimated to have killed between 40 million and 50 million people worldwide.

Health authorities further are warning that it is not a matter of if, but when, where, and how seriously humans will be affected by an avian flu virus. The magnitude of the threat, not just to a particular country but to individuals, warrants a massive campaign to avoid bird-to-bird transmission and to avoid or inhibit human-to-human transmission of an avian flu virus. Therefore, countries around the world have taken preventive measures against a potential outbreak of avian flu, in particular, by destroying infected birds and birds that may be infected. However, a crucial part of this entire effort is individual responsibility.

From current evidence, individuals fall victim to an avian flu virus through contact with infected birds, such as chickens, turkeys, ducks, and migratory birds, for example. To date, there is little or no evidence that an avian flu virus is spread through human-to-human transmission. However, a few isolated cases have been reported of people believed to have been infected by avian flu from a person infected with the virus. Therefore, individuals most at risk of infection are those who work on poultry farms, in poultry markets, and in poultry processing plants. Furthermore, the general population may be at risk because the avian flu virus is not killed or inactivated by freezing processed fowl. Influenza also has been shown to remain infectious on nonporous surfaces for 24 to 48 hours. Recent data from the World Health Organization Laboratory has shown that H5N1 can survive in the environment for six days at 37° C. Therefore, a potential exists for individuals to be infected with avian flu virus from processed, infected fowl.

Presently, the greatest health concern centers on a strain of avian flu virus known as H5N1, a lethal form of the avian flu virus. Although, over 100 subtypes of avian flu have been identified, avian flu types normally only infect birds, and in rare instances, pigs. H5N1 is the only strain of avian flu within the H5 subtype known to infect humans.

The first documented human infection attributed H5N1 avian influenza virus occurred in 1997 in Hong Kong. The steps the government took to cull birds and stop the spread of avian flu may well have prevented the progression of the virus to mutate to allow transmission by human-to-human contact spread. But as long as the H5N1 virus continues to circulate in birds, opportunities exist for this virus to adapt and infect to humans.

Therefore, avian flu virus contamination of skin and environmental surfaces should be minimized to reduce the risk of transmitting the infection to the general population. The risk of transmitting such avian flu viral infections, and all other influenza infections, can be reduced significantly by inactivating or removing the viruses from the hands, other animate surfaces, and inanimate surfaces.

It is known that washing body parts (e.g., hand washing) and hard surfaces (e.g., countertops and sinks) can significantly decrease the population of microorganisms, including pathogens. Therefore, cleaning skin and other animate and inanimate surfaces to reduce microbial populations is a first defense in removing such pathogens from these surfaces, and thereby minimizing the risk of infection.

Common household phenol/alcohol disinfectants are effective in disinfecting contaminated environmental surfaces, but lack persistent virucidal activity. Hand washing is highly effective in disinfecting contaminated fingers, but again suffers from a lack of persistent activity. These shortcomings illustrate the need for improved virucidal compositions having a persistent activity against viruses, such as influenza viruses, including avian flu viruses.

Antimicrobial personal care compositions are known in the art. In particular, antibacterial cleansing compositions, which typically are used to cleanse the skin and destroy bacteria present on the skin, especially the hands, arms, and face of the user, are well-known commercial products.

Antibacterial compositions are used, for example, in the health care industry, food service industry, meat and fowl processing industries, and in the private sector by individual consumers. The widespread use of antibacterial compositions indicates the importance consumers place on controlling bacteria populations on skin. The paradigm for antibacterial compositions is to provide a substantial and broad spectrum reduction in bacterial populations quickly and without adverse side effects associated with toxicity and skin irritation. Such antibacterial compositions are disclosed in U.S. Pat. Nos. 6,107,261 and 6,136,771, each incorporated herein by reference.

One class of antibacterial personal care compositions is the hand sanitizers. This class of compositions is used primarily by medical personnel to disinfect the hands and fingers. A hand sanitizer is applied to, and rubbed into, the hands and fingers, and the composition is allowed to evaporate from the skin.

Hand sanitizers contain a high percentage of an alcohol, like ethanol. At the high percent of alcohol present in the gel, the alcohol itself acts as a disinfectant. In addition, the alcohol quickly evaporates to obviate wiping or rinsing skin treated with the sanitizer gel. Hand sanitizers containing a high percentage of an alcohol, i.e., about 40% or greater by weight of the composition, do not provide a persistent microbial kill.

Antibacterial cleansing compositions typically contain an active antibacterial agent, a surfactant, and various other ingredients, for example, dyes, fragrances, pH adjusters, thickeners, skin conditioners, and the like, in an aqueous and/or alcoholic carrier. Several different classes of antibacterial agents have been used in antibacterial cleansing compositions. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'-hydroxy-diphenylether). Antimicrobial compositions based on such antibacterial agents exhibit a wide range of antibacterial activity, ranging from low to high, depending on the microorganism to be controlled and the particular antibacterial composition. Most commercial antibacterial compositions generally offer a low to moderate antibacterial activity, and no reported antiviral activity.

Antimicrobial activity is assessed against a broad spectrum of microorganisms, including Gram positive and Gram negative microorganisms. The log reduction, or alternatively the percent reduction, in microbial populations provided by the antimicrobial composition correlates to antimicrobial efficacy. A 1-3 log reduction is preferred, a log reduction of 3-5 is most preferred, whereas a log reduction of less than 1 is least preferred, for a particular contact time, generally ranging from 15 seconds to 5 minutes. Thus, a highly preferred antimicrobial composition exhibits a 3-5 log reduction against a broad spectrum of microorganisms in a short contact time.

Virus control poses a more difficult problem than bacterial control. By sufficiently reducing bacterial populations, the risk of bacterial infection is reduced to acceptable levels. Therefore, a rapid antibacterial kill is desired. With respect to viruses, however, not only is a rapid kill desired, but a persistent antiviral activity also is required. This difference is because merely reducing a virus population is insufficient to reduce infection. In theory, a single virus can cause infection. Therefore, an essentially total, and persistent, antiviral activity is required, or at least desired, for an effective antiviral cleansing composition.

WO 98/01110 discloses compositions comprising triclosan, surfactants, solvents, chelating agents, thickeners, buffering agents, and water. WO 98/01110 is directed to reducing skin irritation by employing a reduced amount of surfactant.

U.S. Pat. No. 5,635,462 discloses compositions comprising PCMX and selected surfactants. The compositions disclosed therein are devoid of anionic surfactants and nonionic surfactants.

EP 0 505 935 discloses compositions containing PCMX in combination with nonionic and anionic surfactants, particularly nonionic block copolymer surfactants.

WO 95/32705 discloses a mild surfactant combination that can be combined with antibacterial compounds, like triclosan.

WO 95/09605 discloses antibacterial compositions containing anionic surfactants and alkylpolyglycoside surfactants.

WO 98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

N. A. Allawala et al., *J. Amer. Pharm. Assoc.—Sci. Ed., Vol. XLII*, no. 5, pp. 267-275 (1953) discusses the antibacterial activity of active antibacterial agents in combination with surfactants.

A. G. Mitchell, *J. Pharm. Pharmacol., Vol.* 16, pp. 533-537 (1964) discloses compositions containing PCMX and a nonionic surfactant that exhibit antibacterial activity.

U.S. Pat. No. 6,110,908 discloses a topical antiseptic containing a $C_{2-3}$ alcohol, a free fatty acid, and zinc pyrithione.

U.S. Pat. No. 5,776,430 discloses a topical antimicrobial cleaner containing chlorhexidine and an alcohol. The compositions contain about 50% to 60%, by weight, denatured alcohol and about 0.65% to 0.85%, by weight, chlorhexidine. The composition is applied to the skin, scrubbed into the skin, then rinsed from the skin.

European Patent Application 0 604 848 discloses a gel-type hand disinfectant containing an antimicrobial agent, 40% to 90% by weight of an alcohol, and a polymer and a thickening agent in a combined weight of not more than 3% by weight. The gel is rubbed into the hands and allowed to evaporate to provide disinfected hands. The disclosed compositions often do not provide immediate sanitization and do not provide persistent antimicrobial efficacy.

In general, hand sanitizer gels typically contain: (a) at least 60% by weight ethanol or a combination of lower alcohols, such as ethanol and isopropanol, (b) water, (c) a gelling polymer, such as a crosslinked polyacrylate material, and (d) other ingredients, such as skin conditioners, fragrances, and the like. Hand sanitizer gels are used by consumers to effectively sanitize the hands, without, or after, washing with soap and water, by rubbing the hand sanitizer gel on the surface of the hands. Current commercial hand sanitizer gels rely on high levels of alcohol for disinfection and evaporation, and thus suffer from disadvantages. Specifically, because of the volatility of ethanol, the primary antimicrobial agent does not remain on the skin after use, thus failing to provide a persistent antimicrobial effect.

At alcohol concentrations below 60%, ethanol is not recognized as an antiseptic. Thus, in compositions containing less than 60% alcohol, an additional antimicrobial compound is present to provide antimicrobial activity. Prior disclosures, however, have not addressed the issue of which composition ingredient in such an antimicrobial composition provides microbe control. Therefore, for formulations containing a reduced alcohol concentration, the selection of an antimicrobial agent that provides both a rapid antimicrobial effect and a persistent antimicrobial benefit is difficult.

U.S. Pat. Nos. 6,107,261 and 6,136,771 disclose highly effective antibacterial compositions containing a phenolic antimicrobial agent. These patents disclose compositions that solve the problem of controlling bacteria on skin and hard surfaces, but are silent with respect to controlling viruses.

U.S. Pat. Nos. 5,968,539; 6,106,851; and 6,113,933 disclose antibacterial compositions having a pH of about 3 to about 6. The compositions contain an antibacterial agent, an anionic surfactant, and a proton donor.

Antiviral compositions disclosed as inactivating or destroying pathogenic viruses, including rhinovirus, rotavirus, influenza virus, parainfluenza virus, respiratory syncytial virus, and Norwalk virus, also are known. For example, U.S. Pat. No. 4,767,788 discloses the use of glutaric acid to inactivate or destroy viruses. U.S. Pat. No. 4,975,217 discloses compositions containing an organic acid and an anionic surfactant, for formulation as a soap or lotion, to control viruses. U.S. Patent Publication 2002/0098159 discloses the use of a proton donating agent and a surfactant, including an antibacterial surfactant, to effect antiviral and antibacterial properties.

U.S. Pat. No. 6,034,133 discloses a virucidal hand lotion containing malic acid, citric acid, and a $C_{1-6}$ alcohol. U.S. Pat. No. 6,294,186 discloses combinations of a benzoic acid analog, such as salicyclic acid, and selected metal salts as being effective against viruses, including rhinovirus. U.S. Pat. No. 6,436,885 discloses a combination of known antibacterial agents with 2-pyrrolidone-5-carboxylic acid, at a pH of 2 to 5.5, to provide antibacterial and antiviral properties.

Organic acids in personal washing compositions also have been disclosed. For example, WO 97/46218 and WO 96/06152 disclose the use of organic acids or salts, hydrotropes, triclosan, and hydric solvents in a surfactant base for antimicrobial cleansing compositions. These publications are silent with respect to antiviral properties.

Hayden et al., *Antimicrobial Agents and Chemotherapy,* 26:928-929 (1984), discloses interrupting the hand-to-hand transmission of rhinovirus colds through the use of a hand lotion having residual virucidal activity. The hand lotions, containing 2% glutaric acid, were more effective than a placebo in inactivating certain types of rhinovirus. However, the publication discloses that the glutaric acid-containing lotions were not effective against a wide spectrum of rhinovirus serotypes.

A virucidal tissue designed for use by persons infected with the common cold, and including citric acid, malic acid, and sodium lauryl sulfate, is known. Hayden et al., *Journal of Infectious Diseases,* 152:493-497 (1985), however, reported that use of paper tissues, either treated with virus-killing substances or untreated, can interrupt the hand-to-hand transmission of viruses. Hence, no distinct advantage in preventing the spread of rhinovirus colds can be attributed to the compositions incorporated into the virucidal tissues.

An efficacious antimicrobial composition effective against influenza viruses in general, and avian flu viruses in particular, is needed in the art. Such a composition would be effective in stemming the transmission of influenza viruses, and particularly highly pathogenic avian flu viruses from a contaminated source, like a bird, to a human when the infected, or potentially infected, human regularly uses the composition during or after contacting, processing, or working with the virus-contaminated source, such as fowl. Protectable humans, for example, include persons who work on poultry farms and in poultry processing plants. In the case an avian flu virus mutates and enables human-to-human contamination, such a product would be needed to inhibit the transmission of the avian flu virus throughout the population.

Although a number of antimicrobial cleansing products currently exist, taking a variety of product forms (e.g., deodorant soaps, hard surface cleaners, and surgical disinfectants), such antimicrobial products typically incorporate antimicrobial agents, e.g., a phenolic compound, and/or harsh surfactants, which can dry out and irritate skin tissues. Ideally, personal cleansing products gently cleanse the skin, cause little or no irritation, and do not leave the skin overly dry after frequent use.

Accordingly, a need exists for an antimicrobial composition that is highly efficacious against influenza viruses, and particularly avian flu viruses, in a short time period, and wherein the composition can provide a persistent antiviral activity and is mild to the skin. Personal care products demonstrating improved mildness and a heightened level of influenza virus reduction are provided by the antimicrobial compositions of the present invention.

SUMMARY OF THE INVENTION

The present invention is directed to antimicrobial compositions that provide a rapid and a persistent antiviral effectiveness, and particularly a rapid and persistent activity against influenza viruses, including an avian flu virus, in less than about one minute. More particularly, the present invention relates to antimicrobial compositions containing (a) a disinfecting alcohol, (b) an organic acid, and (c) water, wherein the composition has a pH of about 5 or less. In preferred embodiments, the composition is capable of providing a residual layer comprising the organic acid on a treated surface. A present composition also can contain cleansing surfactants, such as anionic, cationic, and ampholytic surfactants, and active antibacterial agents, such as phenolic and quaternary ammonium antibacterial agents.

The present invention helps protect individuals against infection by an influenza virus, including avian flu virus strains that are capable of bird-to-human or human-to-human transmission, i.e., a strain that will spread geometrically or exponentially within a given human population without necessarily requiring physical contact. An individual also can be protected against viral strains that infect and cause disease in humans, but that are transmitted by birds rather than other humans.

Regardless of the log P of the organic acid, a present antimicrobial composition provides a rapid and persistent control of an influenza virus, including the pathogenic H5 influenza subtype. In one embodiment, the organic acid has a water-octanol partition coefficient, expressed as log P, of less than one, and the composition exhibits a substantial activity against influenza viruses. An organic acid having a log P of one or greater provides a composition exhibiting an activity against bacteria. In yet another embodiment, the organic acid comprises a first organic acid having a log P less than one and an organic acid having a log P of one or greater, and the composition exhibits activity against both influenza viruses and bacteria.

Accordingly, one aspect of the present invention is to provide an antimicrobial composition that is highly effective at killing a broad spectrum of bacteria, including Gram positive and Gram negative bacteria such as *S. aureus, S. choleraesuis, E. coli*, and *K. pneumoniae*, while simultaneously inactivating or destroying influenza viruses, including avian flu viruses harmful to human health, particularly the H5 influenza subtype, and especially H5N1.

The present invention also inhibits the transmission of other influenza viruses. The invention is particularly useful in inhibiting transmission and protecting against infection by pandemic, emerging pandemic, and future pandemic avian flu virus strains, e.g., protecting against H5 influenza subtypes. The present invention also can inhibit transmissions of other hemagglutinin viral subtypes, including H1, H2, H3, H4, H6, H7, H8, H9, H10, H11, H12, H13, H14, H15, and H16. The present invention also can inhibit transmission of neuramidose viral subtypes, including N1, N2, N3, N4, N5, N6, N7, N8, and N9.

Another aspect of the present invention is to provide a liquid, antimicrobial composition capable of inactivating or killing influenza viruses comprising:

(a) about 25% to 75%, by weight, of a disinfecting alcohol, like a $C_{1-6}$ alcohol;

(b) a virucidally effective amount of one or more organic acid; and (c) water, wherein the composition has a pH of about 5 or less.

In preferred embodiments, the composition provides an essentially continuous layer or film comprising the organic acid on a treated surface to impart a persistent antiviral activity to the treated surface. In other preferred embodiments, the composition is free of an intentionally-added surfactant. In further preferred embodiments, the composition comprises a gelling agent.

Yet another aspect of the present invention is to provide an antimicrobial composition that exhibits a persistent control against influenza viruses, including avian flu virus strains.

Another aspect of the present invention is to provide an antimicrobial composition having antiviral activity and comprising (a) a disinfecting alcohol and (b) an organic acid that is substantive to the skin, and/or that fails to penetrate the skin, and/or that resists rinsing from the skin, and/or that forms an essentially continuous barrier layer on the skin, for example, hydrophobic monocarboxylic acids, polycarboxylic acids, polymeric acids having a plurality of carboxylic, phosphate, sulfonate, and/or sulfate moieties, or mixtures thereof, and (c) water, wherein the composition has a pH of about 5 or less. Such organic acids typically have a log P of less than one, and the compositions exhibit a substantial activity against influenza viruses and are effective against a broad spectrum of bacteria. The persistent antiviral activity is attributed, in part, to a residual layer or film of the organic acid on a treated surface, which resists removal from the skin after several rinsings, and during normal daily routines for a period of several hours.

Preferred compositions comprise one or more polycarboxylic acid, a polymeric acid, and a gelling agent. These compositions provide an effective and persistent control of influenza viruses and exhibit a synergistic activity against Gram positive and Gram negative bacteria.

Another aspect of the present invention is to provide an antimicrobial composition that exhibits a substantial, and preferably persistent, control of influenza viruses, and has a pH of about 2 to about 5.

Yet another aspect of the present invention is to provide an antimicrobial composition that exhibits a log reduction against Gram positive bacteria (i.e., *S. aureus*) of at least 2 after 30 seconds of contact.

Still another aspect of the present invention is to provide an antimicrobial composition that exhibits a log reduction against Gram negative bacteria (i.e., *E. coli*) of at least 2.5 after 30 seconds of contact.

Another aspect of the present invention is to provide an antimicrobial composition that exhibits a log reduction against avian flu viruses, such as the H5 subtype, including the H5N1 strain, of at least 4 after 30 seconds of contact. The antimicrobial composition also provides a log reduction against avian flu viruses of about 3 for at least about five hours, and at least 2 for about six hours, after application with a 30 second contact time. In some embodiments, the antimicrobial composition provides a log reduction of 2 against avian flu viruses for up to about eight hours.

Another aspect of the present invention is to provide an antimicrobial composition that resists rinsing from the skin, e.g., at least 50%, at least 60%, and preferably at least 70% of the nonvolatile components of an applied composition remains on a treated surface after three water rinsings and an effective antiviral amount of the composition remains on the skin after ten water rinsings.

Another aspect of the present invention is to provide consumer products based on an antimicrobial composition of the present invention, for example, a skin cleanser, a body splash, a surgical scrub, a wound care agent, a hand sanitizer, a disinfectant, an inanimate surface sanitizer, a lotion, an ointment, a cream, and the like. A composition of the present invention can be a rinse-off product or a leave-on product. Preferably, the composition is allowed to remain on the skin to allow the volatile components of the composition evaporate and provide an essentially continuous residual film or layer of the nonvolatile composition components, e.g., the organic acid, on the skin. The compositions are esthetically pleasing and nonirritating to the skin.

A further aspect of the present invention is to provide a method of quickly controlling influenza viruses on animal tissue, including human tissue, by contacting the tissue, like the dermis, with a composition of the present invention for a sufficient time, for example, about 15 seconds to 5 minutes or longer, e.g., about one hour, to reduce influenza virus populations to a desired level. A further aspect of the present invention is to provide a composition that provides a persistent control of influenza viruses, including avian flu viruses, on animal tissue.

Still another aspect of the present invention is to provide a method preventing transmission of avian flu virus-mediated diseases and conditions from both animate and inanimate surfaces.

Yet another aspect of the present invention is to provide a composition and method of interrupting transmission of an influenza virus from an animate source, e.g., a bird or a human, or an inanimate surface to an animate surface, especially human skin. Especially provided is a method and composition for controlling the transmission of avian flu viruses, particularly the H5N1 strain, by effectively controlling viruses present on human skin and continuing to control the viruses for a period of about four or more hours, and up to about eight hours, after application of the composition to the skin.

These and other novel aspects and advantages of the present invention are set forth in the following, nonlimiting detailed description of the preferred embodiments.

DETAILED DESCRIPTION OF THE PREFERRED EMBODIMENTS

Figure 1A:
FIGS. 1*a* and 1*b* are reflectance micrographs showing a barrier layer of nonvolatile components on a surface provided by application of a composition of the present invention to the surface.

Personal care products incorporating an active antimicrobial agent have been known for many years. Since the introduction of antimicrobial personal care products, many claims have been made that such products provide antimicrobial properties. To be most effective, an antimicrobial composition should provide a high log reduction against a broad spectrum of organisms in as short a contact time as possible. Ideally, the composition also should inactivate viruses.

As presently formulated, most commercial liquid antibacterial soap compositions provide a poor to marginal time kill efficacy, i.e., rate of killing bacteria. These compositions do not effectively control viruses.

Antimicrobial hand sanitizer compositions typically do not contain a surfactant and rely upon a high concentration of an alcohol to control bacteria. The alcohols evaporate and, therefore, cannot provide a persistent bacterial control. The alcohols also can dry and irritate the skin.

Most current products especially lack efficacy against Gram negative bacteria, such as *E. coli*, which are of particular concern to human health. Compositions do exist, however, that have an exceptionally high broad spectrum antibacterial efficacy, as measured by a rapid kill of bacteria (i.e., time kill), which is to be distinguished from persistent kill. These products also lack a sufficient antiviral activity.

The present antimicrobial compositions provide excellent antiviral and antibacterial efficacy and significantly improve antiviral efficacy against influenza viruses compared to prior compositions that incorporate a high percentage of an alcohol, i.e., 40% or greater, by weight. The basis of this improved efficacy is (a) the discovery that a combination of a disinfecting alcohol and an organic acid, and especially an organic acid having a log P of less than about 1, substantially improves antiviral efficacy against an influenza virus, and (b) the pH of a surface after application of the composition to the surface.

An important aspect of the present invention is to maintain a low skin pH for an extended time to provide a persistent antiviral activity. In preferred embodiments, this is achieved by forming an essentially continuous film of the nonvolatile composition components on the skin, which provides a reservoir of the organic acids to maintain a low skin pH.

The term "essentially continuous film" means that a residue of the nonvolatile components of the composition in the form of a barrier layer is present on at least 50%, at least 60%, at least 70%, or at least 80%, preferably at least 85% or at least 90%, and more preferably at least 95%, of the area of the treated surface area. An "essentially continuous" film is demonstrated in the reflectance micrographs of the figures, which are discussed hereafter. The term "essentially continuous film" as used herein is synonymous with the term "essentially continuous layer", "barrier layer", and "barrier film".

A disinfecting alcohol and an organic acid having a log P of less than one act synergistically to control avian flu viruses. A disinfecting alcohol and an organic acid having a log P of one or greater act synergistically to substantially improve antibacterial efficacy. A combination of a first organic acid having a log P less than one and a second organic acid having a log P of one or greater, with a disinfecting alcohol, provides a synergistic improvement in the control of influenza viruses and Gram positive and Gram negative bacteria.

Although compositions containing an antimicrobial agent, like triclosan, have demonstrated a rapid and effective antibacterial activity against Gram positive and Gram negative bacteria, control of viruses has been inadequate. Virus control on skin and inanimate surfaces is very important in controlling the transmission of numerous diseases, and particularly in controlling avian influenza.

Because of the lethality of certain avian flu viruses to infected individuals, it is important that a composition having antiviral activity is active against avian flu viruses, and particularly the H5N1 strain. Although the molecular biology of influenza viruses is understood, finding effective methods for preventing disease caused by influenza viruses, including avian flu viruses, and for preventing the spread of the influenza virus to noninfected subjects, and particularly humans, has been fruitless.

The most common mode of transmitting avian flu virus is bird-to-bird or bird-to-human, but person-to-person transmission through contaminated hands or through contact with contaminated surfaces is feared. It is known that washing hands and hard surfaces with soap and/or other cleansers may not kill a virus, but helps prevent its spread. Because no other effective way to eliminate many viruses, or the spread of viruses, is currently available, workers in contact with birds must adhere to strict hygienic practices to help curtail the spread of avian flu virus. An improved composition having enhanced antiviral efficacy, including persistent antiviral efficacy, in inactivating avian flu viruses would further curtail the spread of avian flu virus infections.

Virucidal means capable of inactivating or destroying a virus. As used herein, the term "persistent antiviral efficacy" or "persistent antiviral activity" means leaving a residue or imparting a condition on animate (e.g., skin) or inanimate surfaces that provides significant antiviral activity for an extended time after application. In some embodiments, a "persistent antiviral efficacy" or "persistent antiviral activity" means leaving a barrier residue or film of antiviral agents, including organic acids, on animate (e.g., skin) or inanimate surfaces that provides significant antiviral activity for an extended time after application. The barrier residue or film can be continuous or essentially continuous, and resists removal from a treated surface during water rinsing.

A composition of the present invention provides a persistent antiviral efficacy, i.e., preferably a log reduction of at least 3, and more preferably a log reduction of at least log 4, against influenza viruses, i.e., H1 through H16 and N1 through N9, including H5 viruses, such as H5N1 virus strains, within 30 seconds of contact with the composition. Antiviral activity is maintained for at least about 0.5 hour, preferably at least about one hour, and more preferably for at least about two hours, at least about three hours, or at least about four hours after contact with the composition. In some preferred embodiments, antiviral activity is maintained for about six to about eight hours after contact with the composition. In some embodiments, the persistent antiviral activity is attributed, at least in part, to the reservoir of organic acids present in the barrier layer or film of the composition on a treated surface. The methodology utilized to determine a persistent antiviral efficacy is discussed below.

The antimicrobial compositions of the present invention are highly effective in providing a rapid and broad spectrum control of bacteria, and a rapid and persistent control of influenza viruses. The highly effective compositions comprise (a) a disinfecting alcohol and (b) a virucidally effective amount of an organic acid. Preferred embodiments comprise at least one of a polymeric acid and a gelling agent. Other preferred embodiments comprise a polymeric acid and a gelling agent.

The disinfecting alcohol and an organic acid having a log P of less than about 1 act synergistically to control influenza viruses. The disinfecting alcohol and an organic acid having a log P of 1 or greater act synergistically to control a broad spectrum of bacteria. A composition containing a first organic acid having a log P of less than one and a second organic acid having a log P of one or greater act synergistically to control influenza viruses and a broad spectrum of Gram positive and Gram negative bacteria.

The compositions are surprisingly mild to the skin, and noncorrosive to inanimate surfaces. Thus, mild and effective compositions that solve the problem of bacteria and influenza virus control are provided to consumers.

The present compositions provide an effective and persistent inactivation of influenza viruses. Influenza viruses include, but are not limited to, H1, H2, H3, H4, H5, H6, H7, H8, H9, H10, H11, H12, H13, H14, H15, H16, N1, N2, N3, N4, N5, N6, N7, N8, and N9 viral subtypes. The compositions are especially effective against the H5 and H7 viral subtype, including the pathogenic H5N1, H5N2, H5N8, H5N9, H7N1, H7N3, H7N4, and H7N7 strains.

The antimicrobial compositions of the present invention are highly efficacious in household cleaning applications (e.g., hard surfaces, like floors, countertops, tubs, dishes, and soft cloth materials, like clothing), personal care applications (e.g., lotions, shower gels, soaps, shampoos, and wipes), and industrial, nursing home, cruise ship, and hospital applications (e.g., sterilization of instruments, medical devices, and gloves). The present compositions efficaciously and rapidly disinfect surfaces that are infected or contaminated with Gram negative bacteria, Gram positive bacteria, and influenza viruses (e.g., H5N1). The present compositions also provide a persistent antiviral effectiveness.

The present compositions can be used in vitro and in vivo. In vitro means in or on nonliving things, especially on inanimate objects having hard or soft surfaces located or used where preventing viral transmission is desired, most especially on objects that contact birds or are touched by human hands. In vivo means in or on animate objects, especially on mammal skin, and particularly on hands.

As illustrated in the following nonlimiting embodiments, an antimicrobial composition of the present invention comprises: (a) about 25% to about 75%, by weight, of a disinfecting alcohol; (b) a virucidally effective amount of an organic acid; and (c) water. The compositions have a pH of less than about 5. In preferred embodiments, the composition contains an optional gelling agent.

The compositions typically are capable of forming an essentially continuous film or layer of nonvolatile composition ingredients on a treated surface. The film or layer resists removal from the treated surface for several hours after application. In particular, an effective amount of composition ingredients remain on a treated surface after ten rinsings, and at least 50%, preferably at least 60%, and more preferably at least 70%, of the nonvolatile composition ingredients remains on a treated surface after three rinsings.

In embodiments wherein skin is treated, "rinsing" means gently rubbing treated skin for about 30 seconds under a moderate flow of tap water having a temperature of about 30° C. to about 40° C., then air drying the skin.

The compositions exhibit a log reduction against influenza viruses, including avian viruses, such as H5N1, of about 1.5, preferably about 2 or about 2.5 and more preferably about 3 after 30 seconds contact, and a log reduction against these influenza viruses of at least 1.5 about four hours after contact, and at least about 1.25 about six to about eight hours after contact. Preferably, the compositions exhibit a log reduction of at least 1.75, at least 2.0, or at least 2.5 about four hours after contact; and at least 1.5, at least 1.75, or at least 2 about six to eight hours after contact. Preferably, the compositions exhibit a log reduction of at least 1.75, at least 2.0, or at least 2.5 about four hours after contact; and at least 1.5, at least 1.75, or at least 2 about six to eight hours after contact.

The compositions exhibit a log reduction against Gram positive bacteria of about 2 after 30 seconds contact. The compositions also exhibit a log reduction against Gram negative bacteria of about 2.5 after 30 seconds contact. The compositions also are mild, and it is not necessary to rinse or wipe the compositions from the skin.

In accordance with the invention, a present antimicrobial composition can further comprise additional optional ingredients disclosed hereafter, like hydrotropes, polyhydric solvents, gelling agents, pH adjusters, vitamins, dyes, skin conditioners, and perfumes. The compositions also can contain cleansing surfactants, like anionic surfactants, and active antimicrobial agents, like phenolic and quaternary ammonium antimicrobial agents.

The following ingredients are present in an antimicrobial composition of the present invention.

A. Disinfecting Alcohol

Antimicrobial compositions of the present invention contain about 25% to about 75%, by weight, of a disinfecting alcohol. Preferred embodiments of the present invention contain about 30% to about 75%, by weight, of a disinfecting alcohol. Most preferred embodiments contain about 30% to about 70%, by weight, of a disinfecting alcohol.

As used herein, the term "disinfecting alcohol" is a water-soluble alcohol containing one to six carbon atoms, i.e., $C_{1-6}$ alcohol. Disinfecting alcohols include, but are not limited to, methanol, ethanol, propanol, and isopropyl alcohol.

B. Organic Acid

A present antimicrobial composition also contains an organic acid in a sufficient amount to control and inactivate influenza viruses and bacteria on a surface contacted by the antimicrobial composition. The organic acid acts synergistically with the disinfecting alcohol to provide a rapid control of influenza viruses, including avian flu viruses, and/or bacteria, and provides a persistent viral control.

In particular, an organic acid is present in the composition in a sufficient amount such that the pH of the animate or inanimate surface contacted by the composition is lowered to degree wherein a persistent viral control is achieved. This persistent viral control is achieved regardless of whether the composition is rinsed from, or allowed to remain on, the contacted surface. The organic acid remains at least partially undissociated in the composition, and remains so when the composition is diluted, or during application and rinsing.

Upon application to a surface, such as human skin, the pH of the surface is sufficiently lowered such that a persistent viral control is achieved. In preferred embodiments, a residual amount of the organic acid remains on the skin, even after a rinsing step, preferably as a film or layer, in order to impart a persistent viral control. However, even if the organic acid is essentially completely rinsed from the surface, the surface pH has been sufficiently lowered to impart a viral control for at least 0.5 hour.

Typically, an organic acid is included in a present composition in an amount of about 0.05% to about 15%, and preferably about 0.1% to about 10%, by weight of the composition. To achieve the full advantage of the present invention, the organic acid is present in an amount of about 0.15% to about 6%, by weight of the composition. In preferred embodiments, a mixture of organic acids is included in the composition. The total amount of organic acid is related to the class of organic acid used, and to the identity of the specific acid or acids used.

An organic acid included in a present antimicrobial composition preferably does not penetrate the surface to which it is applied, e.g., remains on the skin surface as opposed to penetrating the skin and forms a layer of film on the skin, together with other nonvolatile composition ingredients, e.g., an optional gelling agent and/or active antibacterial agent. The organic acid, therefore, preferably is a hydrophobic organic acid.

In one embodiment of the present invention, the organic acid has a log P of less than one, and preferably less than 0.75. To achieve the full advantage of the present invention, the organic acid has a log P of less than 0.5. In this embodiment, the disinfecting alcohol and organic acid act synergistically to provide an effective and persistent viral control.

In another embodiment, the organic acid has a log P of 1 or greater, for example, 1 to about 100. In this embodiment, the disinfecting alcohol and organic acid effectively control influenza viruses and also act synergistically to control a broad spectrum of bacteria.

It is envisioned that, by incorporating a first organic acid having a log P of less than one and a second organic acid having a log P of 1 or greater into a present composition, the first and second organic acids act synergistically with the disinfecting alcohol to provide a persistent control of influenza viruses and a broad spectrum bacteria control.

As used herein, the term "log P" is defined as the log of the water-octanol partition coefficient, i.e., the log of the ratio $P_w/P_o$, wherein $P_w$ is the concentration of an organic acid in water and $P_o$ is the concentration of the organic acid in octanol, at equilibrium and 25° C. The water-octanol coefficient can be determined by the U.S. Environmental Protection Agency Procedure, "OPPTS 830.7560 Partition Coefficient (n-Octanol/Water), Generator Column Method" (1996).

Organic acids having a log P less than one typically are water insoluble, e.g., have a water solubility of less than about 0.5 wt % at 25° C. Organic acids having a log P of one or greater typically are considered water soluble, e.g., have a water solubility of at least 0.5 wt %, at 25° C.

The organic acid can comprise a monocarboxylic acid, a polycarboxylic acid, a polymeric acid having a plurality of carboxylic, phosphate, sulfonate, and/or sulfate moieties, or mixtures thereof. In addition to acid moieties, the organic acid also can contain other moieties, for example, hydroxy groups and/or amino groups. In addition, an organic acid anhydride can be used in a composition of the present invention as the organic acid.

In one embodiment, the organic acid comprises a monocarboxylic acid having a structure $RCO_2H$, wherein R is $C_{1-10}$alkyl, hydroxy$C_{1-6}$alkyl, halo$C_{1-6}$alkyl, phenyl, or substituted phenyl. The alkyl groups can be substituted with phenyl groups and/or phenoxy groups, and these phenyl and phenoxy groups can be substituted or unsubstituted.

Nonlimiting examples of monocarboxylic acids useful in the present invention are acetic acid, propionic acid, octanoic acid, hydroxyacetic acid, lactic acid, benzoic acid, phenylacetic acid, phenoxyacetic acid, zimanic acid, 2-, 3-, or 4-hydroxybenzoic acid, anilic acid, o-, m-, or p-chlorophenylacetic acid, o-, m-, or p-chlorophenoxyacetic acid, and mixtures thereof. Additional substituted benzoic acids are disclosed in U.S. Pat. No. 6,294,186, incorporated herein by reference. Examples of substituted benzoic acids include, but are not limited to, salicyclic acid, 2-nitrobenzoic acid, thiosalicyclic acid, 2,6-dihydroxybenzoic acid, 5-nitrosalicyclic acid, 5-bromosalicyclic acid, 5-iodosalicyclic acid, 5-fluorosalicylic acid, 3-chlorosalicyclic acid, 4-chlorosalicyclic acid, and 5-chlorosalicyclic acid.

In another embodiment, the organic acid comprises a polycarboxylic acid. The polycarboxylic acid contains at least two, and up to four, carboxylic acid groups. The polycarboxylic acid also can contain hydroxy or amino groups, in addition to substituted and unsubstituted phenyl groups.

Nonlimiting examples of polycarboxylic acids useful in the present invention include malonic acid, succinic acid, glutaric acid, adipic acid, terephthalic acid, phthalic acid, pimelic acid, suberic acid, azelaic acid, sebacic acid, fumaric acid, maleic acid, tartaric acid, malic acid, citric acid, maleic acid, aconitic acid, and mixtures thereof.

Anhydrides of polycarboxylic and monocarboxylic acids also are organic acids useful in the present compositions. Preferred anhydrides are anhydrides of polycarboxylic acids, e.g., phthalic anhydride. At least a portion of the anhydride is hydrolyzed to a carboxylic acid because of the pH of the composition. It is envisioned that an anhydride can be slowly hydrolyzed on a surface contacted by the composition, and thereby assist in providing a persistent antiviral activity.

In a third embodiment, the organic acid comprises a polymeric carboxylic acid, a polymeric sulfonic acid, a sulfated polymer, a polymeric phosphoric acid, or mixtures thereof. The polymeric acid has a molecular weight of about 500 g/mol to 10,000,000 g/mol, and includes homopolymers, copolymers, and mixtures thereof. The polymeric acid preferably is capable of forming a substantive film on a surface and has a glass transition temperature, $T_g$, of less than 25° C., preferably less than 20° C., and more preferably less than about 15° C. The glass transition temperature is the temperature at which an amorphous material, such as a polymer, changes from a brittle, vitreous state to a plastic state. The $T_g$ of a polymer is readily determined by persons skilled in the art using standard techniques.

The polymeric acids are uncrosslinked or only very minimally crosslinked. The polymeric acids typically are prepared from ethylenically unsaturated monomers having at least one hydrophilic moiety, such as carboxyl, carboxylic acid anhydride, sulfonic acid, and sulfate. The polymeric acid can contain a comonomer, such as styrene or an alkene, to increase the hydrophobicity of the polymeric acid.

Examples of monomers used to prepare the polymeric organic acid include, but are not limited to:

(a) Carboxyl group-containing monomers, e.g., monoethylenically unsaturated mono- or polycarboxylic acids, such as acrylic acid, methacrylic acid, maleic acid, fumaric acid, crotonic acid, sorbic acid, itaconic acid, ethacrylic acid, α-chloroacrylic acid, α-cyanoacrylic acid, β-methlacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, citraconic acid, mesaconic acid, glutaconic acid, aconitic acid, tricarboxyethylene, and cinnamic acid;

(b) Carboxylic acid anhydride group-containing monomers, e.g., monoethylenically unsaturated polycarboxylic acid anhydrides, such as maleic anhydride; and (c) Sulfonic acid group-containing monomers, e.g., aliphatic or aromatic vinyl sulfonic acids, such as vinylsulfonic acid, allylsulfonic acid, vinyltoluenesulfonic acid, styrenesulfonic acid, sulfoethyl (meth)acrylate, 2-acrylamido-2-methylpropane sulfonic acid, sulfopropyl (meth)acrylate, and 2-hydroxy-3-(meth)acryloxy propyl sulfonic acid.

The polymeric acid can contain other copolymerizable units, i.e., other monoethylenically unsaturated comonomers, well known in the art, as long as the polymer is substantially, i.e., at least 10%, and preferably at least 25%, acid group containing monomer units. To achieve the full advantage of the present invention, the polymeric acid contains at least 50%, and more preferably, at least 75%, and up to 100%, acid group containing monomer units. The other copolymerizable units, for example, can be styrene, an alkene, an alkyl acrylate, or an alkyl methacrylate. The polymeric acid also can be partially neutralized, which assists dispersion of the polymeric acid into a composition. However, a sufficient number of the acid groups remain unneutralized to reduce skin pH and impart a persistent antiviral activity.

A polymeric acid assists in forming a film or layer of residual organic acid on the skin, and assists further in forming a more continuous layer of residual organic acid on the skin. A polymeric acid typically is used in conjunction with a monocarboxylic acid and/or a polycarboxylic acid.

One preferred polymeric acid is a polyacrylic acid, either a homopolymer or a copolymer, for example, a copolymer of acrylic acid and an alkyl acrylate and/or alkyl methacrylate. Another preferred polymeric acid is a homopolymer or a copolymer of methacrylic acid.

Exemplary polymeric acids useful in the present invention include, but are not limited to:

| | |
|---|---|
| Carbomers | (CARBOPOL 910, 934, 934P, 940, 941, ETD 2050; ULTREZ 10, 21) (CARBOPOL ETD 2050) |
| Acrylates/C20-30 Alkyl Acrylate Crosspolymer | (ULTREZ 20) |
| Acrylates/Beheneth 25 Methacrylate Copolymer | (ACULYN 28) |
| Acrylates/Steareth 20 Methacrylate Copolymer | (ACULYN 22) |
| Acrylates/Steareth 20 Methacrylate Crosspolymer | (ACULYN 88) |
| Acrylates Copolymer | (CAPIGEL 98) |
| Acrylates Copolymer | (AVALURE AC) |
| Acrylates/Palmeth 25 Acrylate Copolymer | (SYNTH2000) |
| Ammonium Acrylate Copolymers | |
| Sodium Acrylate/Vinyl Alcohol Copolymer | |
| Sodium Polymethacrylate | |
| Acrylamidopropyltrimonium Chloride/Acrylates Copolymer | |
| Acrylates/Acrylamide Copolymer | |
| Acrylates/Ammonium Methacrylate Copolymer | |
| Acrylates/C10-30 Alkyl Acrylate Crosspolymer | |
| Acrylates/Diacetoneacrylamide Copolymer | |
| Acrylates/Octylacrylamide Copolymer | |
| Acrylates/VA Copolymer | |
| Acrylic Acid/Acrylonitrogens Copolymer | |

In a preferred embodiment of the present invention, the organic acid comprises one or more polycarboxylic acid, e.g., citric acid, malic acid, tartaric acid, or a mixture of any two or all three of these acids, and a polymeric acid containing a plurality of carboxyl groups, for example, homopolymers and copolymers of acrylic acid or methacrylic acid.

C. Carrier

The carrier of the present antimicrobial composition comprises water.

D. Optional Ingredients

An antimicrobial composition of the present invention also can contain optional ingredients well known to persons skilled in the art. The particular optional ingredients and amounts that can be present in the composition are discussed hereafter.

The optional ingredients are present in a sufficient amount to perform their intended function and not adversely affect the antimicrobial efficacy of the composition, and in particular not adversely affect the synergistic effect provided by the disinfecting alcohol and organic acid. Optional ingredients typically are present, individually or collectively, from 0% to about 50%, by weight of the composition.

Classes of optional ingredients include, but are not limited to, hydrotropes, polyhydric solvents, gelling agents, cleansing surfactants, active antibacterial agents, dyes, fragrances, pH adjusters, thickeners, viscosity modifiers, chelating agents, skin conditioners, emollients, preservatives, buffering agents, antioxidants, chelating agents, opacifiers, and similar classes of optional ingredients known to persons skilled in the art.

A hydrotrope, if present at all, is present in an amount of about 0.1% to about 30%, and preferably about 1% to about 20%, by weight of the composition. To achieve the full advantage of the present invention, a composition can contain about 2% to about 15%, by weight, of a hydrotrope.

A hydrotrope is a compound that has an ability to enhance the water solubility of other compounds. A hydrotrope utilized in the present invention lacks surfactant properties, and typically is a short-chain alkyl aryl sulfonate. Specific examples of hydrotropes include, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, sodium camphor sulfonate, and disodium succinate.

A polyhydric solvent, if present at all, is present in an amount of about 0.1% to about 30%, and preferably about 5% to about 30%, by weight of the composition. To achieve the full advantage of the present invention, the polyhydric solvent is present in an amount of about 10% to about 30% by weight of the composition. In contrast to a disinfecting alcohol, a polyhydric solvent contributes minimally, if at all, to the antimicrobial efficacy of the present composition.

The term "polyhydric solvent" as used herein is a water-soluble organic compound containing two to six, and typically two or three, hydroxyl groups. The term "water-soluble" means that the polyhydric solvent has a water solubility of at least 0.1 g of polyhydric solvent per 100 g of water at 25° C. There is no upper limit to the water solubility of the polyhydric solvent, e.g., the polyhydric solvent and water can be soluble in all proportions.

The term polyhydric solvent, therefore, encompasses water-soluble diols, triols, and polyols. Specific examples of hydric solvents include, but are not limited to, ethylene glycol, propylene glycol, glycerol, diethylene glycol, dipropylene glycol, tripropylene glycol, hexylene glycol, butylene glycol, 1,2,6-hexanetriol, sorbitol, PEG-4, and similar polyhydroxy compounds.

As previously stated, the present compositions also can contain a cleansing surfactant and/or an active antimicrobial agent. A cleansing surfactant can be an anionic, nonionic, or cationic surfactant typically used in personal care and cleaning compositions. An active antimicrobial agent can be a phenolic, e.g., triclosan or PCMX, a bisguanidine, a diphenyl compound, a benzyl alcohol, benzoyl peroxide, hydrogen peroxide, a trihalcarbanilide, a quaternary ammonium compound, or an ethoxylated phenol.

In particular, an antimicrobial agent can be present, if at all, in an amount of 0.1% to about 5%, and preferably about 0.1% to about 2%, and more preferably, about 0.3% to about 1%, by weight of the composition.

Optional antimicrobial agents useful in the present invention are exemplified by the following classes of compounds used alone or in combination:

(1) Phenolic Antimicrobial Agents (a) 2-Hydroxydiphenyl Compounds

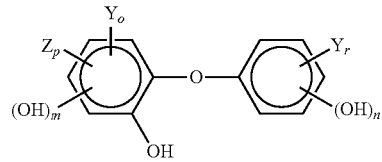

wherein Y is chlorine or bromine, Z is $SO_3H$, $NO_2$, or $C_1$-$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has a structure:

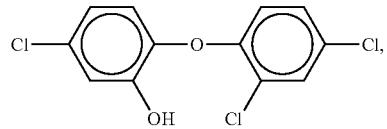

having the adopted name, triclosan, and available commercially under the tradename IRGASAN DP300, from Ciba Specialty Chemicals Corp., Greensboro, N.C. Another useful 2-hydroxydiphenyl compound is 2,2'-dihydroxy-5,5'-dibromo-diphenyl ether.

(b) Phenol Derivatives

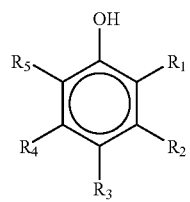

wherein $R_1$ is hydro, hydroxy, $C_1$-$C_4$ alkyl, chloro, nitro, phenyl, or benzyl; $R_2$ is hydro, hydroxy, $C_1$-$C_6$ alkyl, or halo; $R_3$ is hydro, $C_1$-$C_6$ alkyl, hydroxy, chloro, nitro, or a sulfur in the form of an alkali metal salt or ammonium salt; $R_4$ is hydro or methyl; and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in U.S. Pat. No. 6,436,885, incorporated herein by reference.

(c) Diphenyl Compounds

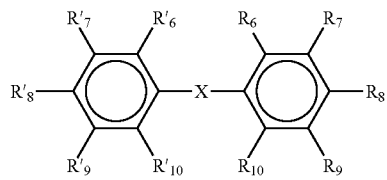

wherein X is sulfur or a methylene group, $R_6$ and $R'_6$ are hydroxy, and $R_7$, $R'_7$, $R_8$, $R'_8$, $R_9$, $R'_9$, $R_{10}$, and $R'_{10}$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine. Other diphenyl compounds are listed in U.S. Pat. No. 6,436,885, incorporated herein by reference.

(2) Quaternary Ammonium Antimicrobial Agents

Useful quaternary ammonium antibacterial agents have a general structural formula:

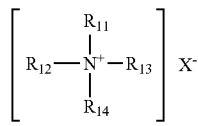

wherein at least one of $R_{11}$, $R_{12}$, $R_{13}$, and $R_{14}$ is an alkyl, aryl, or alkaryl substituent containing 6 to 26 carbon atoms. Alternatively, any two of the R substituents can be taken together, with the nitrogen atom, to form a five- or six-membered aliphatic or aromatic ring. Preferably, the entire ammonium cation portion of the antibacterial agent has a molecular weight of at least 165.

The substituents $R_{11}$, $R_{12}$, $R_{13}$, and $R_{14}$ can be straight chained or can be branched, but preferably are straight chained, and can include one or more amide, ether, or ester linkage. In particular, at least one substituent is $C_6$-$C_{26}$alkyl, $C_6$-$C_{26}$alkoxyaryl, $C_6$-$C_{26}$alkaryl, halogen-substituted $C_6$-$C_{26}$alkaryl, $C_6$-$C_{26}$alkylphenoxyalkyl, and the like. The remaining substituents on the quaternary nitrogen atom other than the above-mentioned substituent typically contain no more than 12 carbon atoms. In addition, the nitrogen atom of the quaternary ammonium antibacterial agent can be present in a ring system, either aliphatic, e.g., piperdinyl, or aromatic, e.g., pyridinyl. The anion X can be any salt-forming anion which renders the quaternary ammonium compound water soluble. Anions include, but are not limited to, a halide, for example, chloride, bromide, or iodide, methosulfate, and ethosulfate.

Preferred quaternary ammonium antimicrobial agents have a structural formula:

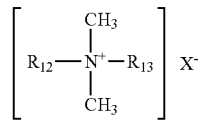

wherein $R_{12}$ and $R_{13}$, independently, are $C_8$-$C_{12}$alkyl, or $R_{12}$ is $C_{12}$-$C_{16}$alkyl, $C_8$-$C_{18}$alkylethoxy, or $C_8$-$C_{18}$alkylphenylethoxy, and $R_{13}$ is benzyl, and X is halo, methosulfate, ethosulfate, or p-toluenesulfonate. The alkyl groups $R_{12}$ and $R_{13}$ can be straight chained or branched, and preferably are linear.

The quaternary ammonium antimicrobial agent in a present composition can be a single quaternary ammonium compound, or a mixture of two or more quaternary ammonium compounds. Particularly useful quaternary ammonium antimicrobial agents include dialkyl($C_8$-$C_{10}$) dimethyl ammonium chlorides (e.g., dioctyl dimethyl ammonium chloride), alkyl dimethyl benzyl ammonium chlorides (e.g., benzalkonium chloride and myristyl dimethylbenzyl ammonium chloride), alkyl methyl dodecyl benzyl ammonium chloride, methyl dodecyl xylene-bis-trimethyl ammonium chloride, benzethonium chloride, dialkyl methyl benzyl ammonium chloride, alkyl dimethyl ethyl ammonium bromide, and an alkyl tertiary amine. Polymeric quaternary ammonium compounds based on these monomeric structures also can be used in the present invention. One example of a polymeric quaternary ammonium compound is POLYQUAT®, e.g., a 2-butenyl dimethyl ammonium chloride polymer. The above quaternary ammonium compounds are available commercially under the tradenames BARDAC®, BTC®, HYAMINE®, BARQUAT®, and LONZABAC®, from suppliers such as Lonza, Inc., Fairlawn, N.J. and Stepan Co., Northfield, Ill.

Additional examples of quaternary ammonium antimicrobial agents include, but are not limited to, alkyl ammonium halides, such as cetyl trimethyl ammonium bromide; alkyl aryl ammonium halides, such as octadecyl dimethyl benzyl ammonium bromide; N-alkyl pyridinium halides, such as N-cetyl pyridinium bromide; and the like. Other suitable quaternary ammonium antimicrobial agents have amide, ether, or ester moieties, such as octylphenoxyethoxy ethyl dimethyl benzyl ammonium chloride, N-(laurylcocoaminoformylmethyl)pyridinium chloride, and the like. Other classes of quaternary ammonium antimicrobial agents include those containing a substituted aromatic nucleus, for example, lauryloxyphenyl trimethyl ammonium chloride, cetylaminophenyl trimethyl ammonium methosulfate, dodecylphenyl trimethyl ammonium methosulfate, dodecylbenzyl trimethyl ammonium chloride, chlorinated dodecylbenzyl trimethyl ammonium chloride, and the like.

Specific quaternary ammonium antimicrobial agents include, but are not limited to, behenalkonium chloride, cetalkonium chloride, cetarylalkonium bromide, cetrimonium tosylate, cetyl pyridinium chloride, lauralkonium bromide, lauralkonium chloride, lapyrium chloride, lauryl pyridinium chloride, myristalkonium chloride, olealkonium chloride, and isostearyl ethyldimonium chloride. Preferred quaternary ammonium antimicrobial agents include benzalkonium chloride, benzethonium chloride, cetyl pyridinium bromide, and methylbenzethonium chloride.

(3) Anilide and Bisguanidine Antimicrobial Agents

Useful anilide and bisguanadine antimicrobial agents include, but are not limited to, triclocarban, carbanilide, salicylanilide, tribromosalan, tetrachlorosalicylanilide, fluorosalan, chlorhexidine gluconate, chlorhexidine hydrochloride, and mixtures thereof.

A surfactant can be included in a composition for lowering skin pH, if at all, in an amount of 0.1% to about 15%, and typically 0.1% to about 10%, by weight, of the composition. More typically, if present at all, the composition contains about 0.1% to about 7%, by weight of the surfactant. The optional surfactant is stable at the pH of the composition and is compatible with the other ingredients present in the composition.

The surfactant can be an anionic surfactant, a cationic surfactant, a nonionic surfactant, or a compatible mixture of surfactants. The surfactant also can be an ampholytic or amphoteric surfactant, which have anionic or cationic properties depending upon the pH of the composition.

The compositions, therefore, can contain an anionic surfactant having a hydrophobic moiety, such as a carbon chain including about 8 to about 30 carbon atoms, and particularly about 12 to about 20 carbon atoms, and further has a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, acyl glutamates, alkyl sulfoacetates, acylated peptides, acyl lactylates, anionic fluoro surfactants, and mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263-266, incorporated herein by reference. Numerous other anionic surfactants, and classes of anionic surfactants, are disclosed in U.S. Pat. No. 3,929,678 and U.S. Patent Publication No. 2002/0098159, each incorporated herein by reference.

Specific, nonlimiting classes of anionic surfactants useful in the present invention include, but are not limited to, a $C_8$-$C_{18}$ alkyl sulfonate, a $C_8$-$C_{18}$ alkyl sulfate, a $C_8$-$C_{18}$ fatty acid salt, a $C_8$-$C_{18}$ alkyl ether sulfate having one or two moles of ethoxylation, a $C_8$-$C_{18}$ alkamine oxide, a $C_8$-$C_{18}$ alkoyl sarcosinate, a $C_8$-$C_{18}$ sulfoacetate, a $C_8$-$C_{18}$ sulfosuccinate, a $C_8$-$C_{18}$ alkyl diphenyl oxide disulfonate, a $C_8$-$C_{18}$ alkyl carbonate, a $C_8$-$C_{18}$ alpha-olefin sulfonate, a methyl ester sulfonate, and mixtures thereof. The $C_8$-$C_{18}$ alkyl group contains eight to eighteen carbon atoms, and can be straight chain (e.g., lauryl) or branched (e.g., 2-ethylhexyl). The cation of the anionic surfactant can be an alkali metal (preferably sodium or potassium), ammonium, $C_1$-$C_4$ alkylammonium (mono-, di-, tri-), or $C_1$-$C_3$ alkanolammonium (mono-, di-, tri-). Lithium and alkaline earth cations (e.g., magnesium) can be used, but are not preferred.

Specific surfactants include, but are not limited to, lauryl sulfates, octyl sulfates, 2-ethylhexyl sulfates, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants. Additional examples of surfactants can be found in CTFA Cosmetic Ingredient Handbook, J. M. Nikitakis, ed., The Cosmetic, Toiletry and Fragrance Association, Inc., Washington, D.C. (1988) (hereafter CTFA Handbook), pages 10-13, 42-46, and 87-94, incorporated herein by reference.

The compositions also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, and mixtures thereof.

Exemplary nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's, at pages 1-246 and 266-272; in the CTFA International Cosmetic Ingredient Dictionary, Fourth Ed., Cosmetic, Toiletry and Fragrance Association, Washington, D.C. (1991) (hereafter the CTFA Dictionary) at pages 1-651; and in the CTFA Handbook, at pages 86-94, each incorporated herein by reference.

In addition to anionic and nonionic surfactants, cationic, ampholytic, and amphoteric surfactants can be used in the compositions. Useful cationic surfactants include those having a structural formula

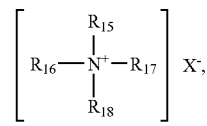

$$\left[ R_{16} - \underset{\underset{R_{18}}{|}}{\overset{\overset{R_{15}}{|}}{N^+}} - R_{17} \right] X^-,$$

wherein $R_{15}$ is an alkyl group having about 12 to about 30 carbon atoms, or an aromatic, aryl, or alkaryl group having about 12 to about 30 carbon atoms; $R_{16}$, $R_{17}$, and $R_{18}$, independently, are selected from the group consisting of hydrogen, an alkyl group having 1 to about 22 carbon atoms, or aromatic, aryl, or alkaryl groups having from about 12 to about 22 carbon atoms; and X is a compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_{15}$, $R_{16}$, $R_{17}$, and $R_{18}$ also can contain ester and/or ether linkages, or hydroxy or amino group substituents (e.g., the alkyl groups can contain polyethylene glycol and polypropylene glycol moieties).

Preferably, $R_{15}$ is an alkyl group having about 12 to about 22 carbon atoms; $R_{16}$ is H or an alkyl group having 1 to about 22 carbon atoms; and $R_{17}$ and $R_{18}$, independently are H or an alkyl group having 1 to about 3 carbon atoms. More preferably, $R_{15}$ is an alkyl group having about 12 to about 22 carbon atoms, and $R_{16}$, $R_{17}$, and $R_{18}$ are H or an alkyl group having 1 to about 3 carbon atoms.

Other useful cationic surfactants include amino-amides, wherein in the above structure $R_{10}$ alternatively is $R_{19}CONH-(CH_2)_n$, wherein $R_{19}$ is an alkyl group having about 12 to about 22 carbon atoms, and n is an integer of 2 to 6, more preferably 2 to 4, and most preferably 2 to 3. Nonlimiting examples of these cationic surfactants include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof.

Additional quaternary ammonium salts include those wherein the $C_{12}$-$C_{30}$ alkyl carbon chain is derived from a tallow fatty acid or from a coconut fatty acid. The term "tallow" refers to an alkyl group derived from tallow fatty acids (usually hydrogenated tallow fatty acids), which generally has mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride.

Ampholytic surfactants, i.e., amphoteric and zwitterionic surfactants, can be broadly described as derivatives of secondary and tertiary amines having straight chain or branched aliphatic radicals, and wherein one of the aliphatic substituents contains from about 8 to about 18 carbon atoms and at least one of the aliphatic substituents contains an anionic water-solubilizing group, e.g., carboxy, sulfonate, or sulfate.

More particularly, one class of ampholytic surfactants include sarcosinates and taurates having the general structural formula

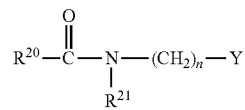

wherein $R^{20}$ is $C_{11}$-$C_{21}$ alkyl, $R^{21}$ is hydrogen or $C_1$-$C_2$ alkyl, Y is $CO_2M$ or $SO_3M$, M is an alkali metal, and n is a number 1 through 3.

Another class of ampholytic surfactants is the amide sulfosuccinates having the structural formula

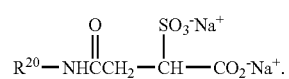

The following classes of ampholytic surfactants also can be used:

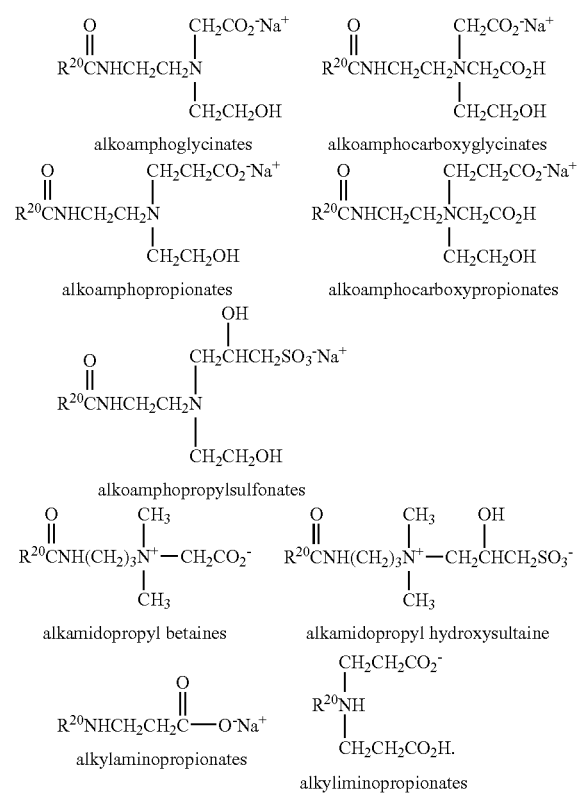

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Useful amphoteric surfactants also include the amine oxides. Amine oxides have a general structural formula wherein the hydrophilic portion contains a nitrogen atom that is bound to an oxygen atom with a semipolar bond.

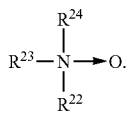

$R^{22}$, $R^{23}$, and $R^{24}$ can be a saturated or unsaturated, branched, or unbranched alkyl or alkenyl group having 1 to about 24 carbon atoms. Preferred amine oxides contain at least one R group that is an alkyl chain of 8 to 22 carbon atoms. Nonlimiting examples of amine oxides include alkyl dimethyl amine oxides, such as decylamine oxide, cocamine oxide, myristamine oxide, and palmitamine oxide. Also useful are the alkylaminopropylamine oxides, for example, coamidopropylamine oxide and stearamidopropylamine oxide.

Nonlimiting examples of preferred surfactants utilized in a composition include those selected from the group consisting of alkyl sulfates; alkyl ether sulfates; alkyl benzene sulfonates; alpha olefin sulfonates; primary or secondary alkyl sulfonates; alkyl phosphates; acyl taurates; alkyl sulfosuccinates; alkyl sulfoacetates; sulfonated fatty acids; alkyl trimethyl ammonium chlorides and bromides; dialkyl dimethyl ammonium chlorides and bromides; alkyl dimethyl amine oxides; alkylamidopropyl amine oxides; alkyl betaines; alkyl amidopropyl betaines; and mixtures thereof. More preferred surfactants include those selected from the group consisting of alkyl sulfates; alkyl ether sulfates; alkyl benzene sulfonates; alpha olefin sulfonates; primary or secondary alkyl sulfonates; alkyl dimethyl amine oxides; alkyl betaines; and mixtures thereof.

The present antimicrobial compositions also can contain, if at all, about 0.01% to about 5%, by weight, and preferably 0.10% to about 3%, by weight, of an optional gelling agent. To achieve the full advantage of the present invention, the antimicrobial compositions contain about 0.25% to about 2.5%, by weight, of a gelling agent. The antimicrobial compositions typically contain a sufficient amount of gelling agent such that the composition is a viscous liquid, gel, or semisolid that can be easily applied to, and rubbed on, the skin or other surface. The optional gelling agent facilitates a uniform application of the composition onto a treated surface and helps provide a more continuous layer or film of nonvolatile composition ingredients on a treated surface. Persons skilled in the art are aware of the type and amount of gelling agent to include in the composition to provide the desired composition viscosity or consistency.

The term "gelling agent" as used here and hereafter refers to a compound capable of increasing the viscosity of a water-based or solvent-based composition, or capable of converting a water-based or solvent-based composition to a gel or semisolid. The gelling agent, therefore, can be organic in nature, for example, a natural gum or a synthetic polymer, or can be inorganic in nature.

The following are nonlimiting examples of gelling agents that can be used in the present invention. In particular, the following compounds, both organic and inorganic, act primarily by thickening or gelling the aqueous portion of the composition:

acacia, agar, algin, alginic acid, ammonium alginate, ammonium chloride, ammonium sulfate, amylopectin, attapulgite, bentonite, $C_{9-15}$ alcohols, calcium acetate, calcium alginate, calcium carrageenan, calcium chloride, caprylic alcohol, carboxymethyl hydroxyethylcellulose, carboxymethyl hydroxypropyl guar, carrageenan, cellulose, cellulose gum, cetearyl alcohol, cetyl alcohol, corn starch, damar, dextrin, dibenzylidine sorbitol, ethylene dihydrogenated tallowamide, ethylene dioleamide, ethylene distearamide, fruit pectin, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyvinyl alcohol, potassium alginate, potassium carrageenan, potassium chloride, potassium sulfate, potato starch, propylene glycol alginate, sodium carboxymethyl dextran, sodium carrageenan, sodium cellulose sulfate, sodium chloride, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, polyvinylpyrrolidone and derivatives thereof, vinyl ether derivatives (methyl vinyl ether, ethyl vinyl ether, butyl vinyl ether, isobutyl vinyl ether, polymethyl vinyl ether/maleic acid), quaternized vinylpyrrolidone/quaternized dimethylamino ethyl pyrrolidone-based polymers and methacrylate copolymers, vinylcaprolactam/vinylpyrrolidone dimethylamino ethylmethacrylate polymers, vinylpyrrolidone/dimethyl amino ethylmethacrylate copolymers, acid stable and naturally occurring derivatives of guar and modified guar, modified or substituted xanthan, carboxypropyl cellulose, and mixtures thereof.

The following additional nonlimiting examples of gelling agents act primarily by thickening the nonaqueous portion of the composition:

abietyl alcohol, acrylinoleic acid, aluminum behenate, aluminum caprylate, aluminum dilinoleate, aluminum distearate, aluminum isostearates/laurates/palmitates or stearates, aluminum isostearates/myristates, aluminum isostearates/palmitates, aluminum isostearates/stearates, aluminum lanolate, aluminum myristates/palmitates, aluminum stearate, aluminum stearates, aluminum tristearate, beeswax, behenamide, behenyl alcohol, butadiene/acrylonitrile copolymer, a $C_{29-70}$ acid, calcium behenate, calcium stearate, candelilla wax, carnauba, ceresin, cholesterol, cholesteryl hydroxystearate, coconut alcohol, copal, diglyceryl stearate malate, dihydroabietyl alcohol, dimethyl lauramine oleate, dodecanedioic acid/cetearyl alcohol/glycol copolymer, erucamide, ethylcellulose, glyceryl triacetyl hydroxystearate, glyceryl triacetyl ricinoleate, glycol dibehenate, glycol dioctanoate, glycol distearate, hexanediol distearate, hydrogenated $C_{6-14}$ olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable glycerides, hydrogenated vegetable oil, hydroxypropylcellulose, isobutylene/isoprene copolymer, isocetyl stearoyl stearate, Japan wax, jojoba wax, lanolin alcohol, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhydride copolymer, octyldodecyl stearoyl stearate, oleamide, oleostearine, ouricury wax, oxidized polyethylene, ozokerite, palm kernel alcohol, paraffin, pentaerythrityl hydrogenated rosinate, pentaerythrityl rosinate, pentaerythrityl tetraabietate, pentaerythrityl tetrabehenate, pentaerythrityl tetraoctanoate, pentaerythrityl tetraoleate, pentaerythrityl tetrastearate, phthalic anhydride/glycerin/glycidyl decanoate copolymer, phthalic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eicosene copolymer, PVP/hexadecene copolymer, rice bran wax, stearalkonium bentonite, stearalkonium hectorite, stearamide, stearamide DEA-distearate, stearamide DIBA-stearate, stearamide MEA-stearate, stearone, stearyl alcohol, stearyl erucamide, stearyl stearate, stearyl stearoyl stearate, synthetic beeswax, synthetic wax, trihydroxystearin, triisononanoin, triisostearin, triisostearyl trilinoleate, trilaurin, trilinoleic acid, trilinolein, trimyristin, triolein, tripalmitin, tristearin, zinc laurate, zinc myristate, zinc neodecanoate, zinc rosinate, zinc stearate, and mixtures thereof.

Exemplary gelling agents useful in the present invention include, but are not limited to,

| | |
|---|---|
| Polyethylene Glycol & Propylene Glycol & Water | (ACULYN 44) |
| Ammonium Acrylatedimethyltaurate/VP Copolymer | (ARISTOFLEX AVC) |
| Glyceryl Stearate & PEG 100 Stearate | (ARLACEL 165) |
| Polyethylene(2)Stearyl Ether | (BRIJ 72) |
| Polyoxyethylene(21)Stearyl Ether | (BRIJ 721) |
| Silica | (CAB-O-SIL) |
| Polyquaternium 10 | (CELQUAT CS230M) |
| Cetyl Alcohol | |
| Cetearyl Alcohol & Ceteareth 20 | (COSMOWAX P) |
| Cetearyl Alcohol & Dicetyl Phosphate & Ceteth-10 Phosphate | (CRODAFOS CES) |
| Ceteth-20 Phosphate & Cetearyl Alcohol & Dicetyl Phosphate | (CRODAFOS CS-20 Acid) |
| Cetearyl Alcohol & Ceteareth 20 | (EMULGADE NI 1000) |
| Sodium Magnesium Silicate | (LAPONITE XLG) |
| Cetyl Alcohol & Stearyl Alcohol & Stearalkonium Chloride & Dimethyl Stearamine & Lactic Acid | (MACKADET CBC) |
| Cetearyl Alcohol & Stearamidopropyldimethylamine & Stearamidopropylalkonium Chloride | (MACKERNIUM Essential) |
| Stearalkonium Chloride | (MACKERNIUM SDC-85) |
| Cetearyl Alcohol & Stearamidopropyldimethylamine & Stearamidopropylalkonium Chloride & Silicone Quaternium 16 | (MACKERNIUM Ultra) |
| Cetearyl Alcohol & Cetearyl Glucoside | (MONTANOV 68EC) |
| Hydroxyethylcellulose | (NATROSOL 250 HHR CS) |
| Polyquaternium-37 & Mineral Oil & Trideceth-6 | (SALCARE SC 95) |
| Polyquaternium-32 & Mineral Oil & Trideceth-6 | (SALCARE SC 96) |
| Stearic Acid | |
| Cetyl Hydroxyethylcellulose | (NATROSOL Plus 330 CS) |
| Polyvinyl Alcohol, PVP-K30, Propylene Glycol | |
| Stearic Acid, Behenyl Alcohol, Glyceryl Stearate, Lecithin, C12-16 Alcohols, Palmic Acid | (PROLIPID 141) |
| Beeswax | (saponified beeswax) |
| Beeswax | (synthetic beeswax) |
| Water, Beeswax, Sesame Oil, Lecithin, Methyl paraben | (beesmilk) |
| Polyquaternium 10 | (CELQUAT SC240C) |
| Sodium Acrylate/Sodium Acrylodimethyl Taurate Copolymer & Isohexadecane & Polysorbate 80 | (SIMULGEL EG) |
| Polyquaternium 44 | (LUVIQUAT Care) |

Other specific classes of optional ingredients include inorganic phosphates, sulfates, and carbonates as buffering agents; EDTA and phosphates as chelating agents; and acids and bases as pH adjusters.

Examples of preferred classes of optional basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of optional acidic pH adjusters are the mineral acids. Nonlimiting examples of mineral acids are hydrochloric acid, nitric acid, phosphoric acid, and sulfuric acid. The identity of the acidic pH adjuster is not limited and any acidic pH adjuster known in the art, alone or in combination, can be used.

The composition also can contain a cosolvent or a clarifying agent, such as a polyethylene glycol having a molecular weight of up to about 4000, methylpropylene glycol, an oxygenated solvent of ethylene, propylene, or butylene, or mixtures thereof. The cosolvent or clarifying agent can be included as needed to impart stability and/or clarity to the composition and may be present in the residual film or layer of the composition on a treated surface.

An optional alkanolamide to provide composition thickening can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof. Alkanolamides are noncleansing surfactants and are added, if at all, in small amounts to thicken the composition.

E. pH

The pH of a present antimicrobial composition is less than about 5, and preferably less than about 4.5 at 25° C. To achieve the full advantage of the present invention, the pH is less than about 4. Typically, the pH of a present composition is about 2 to less than about 5, and preferably about 2.5 to about 4.5.

The pH of the composition is sufficiently low such that at least a portion of the organic acid is in the protonated form. The organic acid then has the capability of lowering surface pH, such as skin pH, to provide an effective viral control, without irritating the skin. The organic acid also deposits on the skin, and resists removal by rinsing, to provide a persistent antiviral effect.

To demonstrate the new and unexpected results provided by the antimicrobial compositions of the present invention, the following examples were prepared, and the ability of the compositions to control influenza viruses, and to control Gram positive and Gram negative bacteria, is determined. The weight percentage listed in each of the following examples represents the actual, or active, weight amount of each ingredient present in the composition. The compositions are prepared by blending the ingredients, as understood by those skilled in the art and as described below.

The following methods are used in the preparation and testing of the examples:

a) Determination of Rapid Germicidal (Time Kill) Activity of Antibacterial Products. The activity of antibacterial compositions is measured by the time kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated.

In general, the time kill method is known to those skilled in the art.

The composition can be tested at any concentration up to 100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about $10^8$ colony forming units per ml (cfu/ml).

The table below lists the test bacterial cultures used in the tests and includes the name of the bacteria, the ATCC (American Type Culture Collection) identification number, and the abbreviation for the name of the organism used hereafter. *S. aureus* is a Gram positive bacteria, whereas *E. coli, K. pneum*, and *S. choler.* are Gram negative bacteria.

| Organism Name | ATCC # | Abbreviation |
|---|---|---|
| *Staphylococcus aureus* | 6538 | *S. aureus* |
| *Escherichia coli* | 11229 | *E. coli* |
| *Klebsiella pneumoniae* | 10031 | *K. pneum.* |
| *Salmonella choleraesuis* | 10708 | *S. choler.* |

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Neutralizer Solution. Decimal dilutions to a countable range then are made. The dilutions can differ for different organisms. Selected dilutions are plated in triplicate on TSA+ plates (TSA+ is Trypticase Soy Agar with Lecithin and Polysorbate 80). The plates then are incubated for 24±2 hours, and the colonies are counted for the number of survivors and the calculation of percent or log reduction. The control count (numbers control) is determined by conducting the procedure as described above with the exception that deionized water is used in place of the test composition. The plate counts are converted to cfu/ml for the numbers control and samples, respectively, by standard microbiological methods.

The log reduction is calculated using the formula

Log reduction=$\log_{10}$(numbers controlled)−$\log_{10}$(test sample survivors).

The following table correlates percent reduction in bacteria population to log reduction:

| % Reduction | Log Reduction |
|---|---|
| 90 | 1 |
| 99 | 2 |
| 99.9 | 3 |
| 99.99 | 4 |
| 99.999 | 5 | b) Antiviral Residual Efficacy Test

References: S. A. Sattar, *Standard Test Method for Determining the Virus-Eliminating Effectiveness of Liquid Hygienic Handwash Agents Using the Fingerpads of Adult Volunteers*, Annual Book of ASTM Standards. Designation E1838-96, incorporated herein by reference in its entirety, and referred to as "Sattar I"; and S. A. Sattar et al., *Chemical Disinfection to Interrupt Transfer of Rhinovirus Type 14 from Environmental Surfaces to Hands*, Applied and Environmental Microbiology, Vol. 59, No. 5, May, 1993, pp. 1579-1585, incorporated herein by reference in its entirety, and referred to as "Sattar II."

The method used to determine the Antiviral Index of the present invention is a modification of that described in Sattar I, a test for the virucidal activity of liquid hand washes (rinse-off products). The method is modified in this case to provide reliable data for leave-on products and for influenza viruses.

Modifications of Sattar I include the product being delivered directly to the skin as described below, influenza virus inoculation of the fingerpads as described below, and viral recovery using five-cycle washing. The inoculated skin site then is completely decontaminated by treating the area with 70% dilution of ethanol in water.

Procedure:

30-minute test:

The subjects (four per test product) first wash their hands with a nonmedicated soap, then the hands were rinsed and allowed to air dry. The hands then were treated with 70% ethanol and air dried. Next, test product (1.8 mL) was applied to the thumb, index, and middle fingers of the hands, and allowed to air dry.

About 30 minutes (±30 seconds) after product application, 10 μl of influenza A virus suspension (approximately $1\times10^6$ $TCID_{50}$/mL) was topically applied to the thumb, index, and middle fingers of the hands. After a dry-down period of 10 minutes, the virus then was eluted from the fingers with 2 mL of eluent (Eagle's Minimal Essential Media (EMEM) with 0.125% bovine Serum Albumin (BSA), 10 mM HEPES, and 1 μg/ML TPCK-treated trypsin)), washing five times per site. The inoculated skin then was completely decontaminated by rinsing the area with 70% ethanol. Viral titers were determined using standard techniques in the art, i.e., $TCID_{50}$ (Tissue Culture Infectious Dose).

Example 1

The following compositions were prepared.

| Sample | Composition (by wt %) |
|---|---|
| 1 | 62% ethanol in water |
| 2 | 2% malic acid in water |
| 3 | 2% citric acid in water |
| 4 | 2% citric acid, 2% malic acid, and 62% ethanol in water |
| 5 | Sterile deionized water |

The samples were tested for antiviral activity against influenza A virus in a time kill suspension test. The following table summarizes the results of the test.

| | Log 10 Reduction of Influenza A Virus | |
|---|---|---|
| Sample | 1 minute | 3 minutes |
| 1 | 3.11 log | >3.5 log |
| 2 | >2.5 log | >2.5 log |
| 3 | >2.5 log | >2.5 log |
| 4 | >1.5 log | >1.5 log |
| 5 | <1 log | <1 log |

This example illustrates the immediate antiviral activity of organic acids and a composition containing organic acids against influenza virus. In Samples 2-4, no viable virus was detected. However, due to cellular toxicity at the lower dilutions, the sensitivity of the test was reduced. Ethanol also has immediate activity against influenza A, although the incubation time was three minutes before complete inactivation of the virus was observed.

Example 2

The following antiviral composition, which is capable of reducing skin pH, was prepared and applied to the fingerpads of human volunteers:

| Sample 2 | |
|---|---|
| Material | Percent (by weight) |
| Ethanol | 62.0 |
| Deionized water | 32.11 |
| ULTREZ ® 10[1)] | 1.0 |
| Citric acid | 2.0 |
| Malic acid | 2.0 |
| Sodium hydroxide | 0.89 |
| | 100.0 |

[1)]Acrylate/C10-30 Alkyl Acrylate Crosspolymer.

The clean fingerpads of test subjects were treated with the above composition. Baseline skin pH readings were measured from the fingerpads prior to treatment with the composition. Skin pH measurements also were taken immediately after the composition dried on the fingerpads, then again 30 minutes after drying.

| Treatment | Average Virus Log 10 Recovered | Viral Log 10 Reduction | % Hands with Virus |
|---|---|---|---|
| Drying Control | 2.67 | | 100 |
| Sample 2 | <1.00 | >1.67 | 0 |

Thirty minutes after treatment of the fingerpads with Sample 2, influenza virus at a titer of $2.5 \times 10^3$ TCID$_{50}$/mL was applied to the fingerpads. The virus was dried on the fingerpads for one minute, then the fingerpads were rinsed with a viral recovery broth containing Eagle's Minimal Essential Media (EMEM) with 0.125% Bovine Serum Albumin (BSA), 10 mM HEPES, and 1 µg/mL TPCK-treated trypsin. The sample was serially diluted in viral recovery broth and plated onto MDCK cells Titers were assayed as per the TCID$_{50}$ method. The drying control demonstrates that influenza virus can survive on the skin for up to one minute and can be recovered from the skin. Sample 2 demonstrates a persistent antiviral activity against influenza virus. Complete inactivation was achieved and a greater than 1.67 log reduction was achieved, compared to virus recovery from untreated fingers contaminated with influenza.

Example 3

Antibacterial Activity

| | Log Reduction | | | |
|---|---|---|---|---|
| | S. aureus ATCC 6538 | | E. coli ATCC 11229 | |
| Sample | 30 seconds[10] | 60 seconds[1)] | 30 seconds | 60 seconds |
| A | >4.91 | >4.91 | >5.00 | >5.00 |
| B | >4.91 | >4.91 | >5.00 | >5.00 |

[1)]Contact time on the skin
A. 62% Ethanol, 2% citric acid, 2% malic acid, 1.25% hydroxyethylcellulose
B. 62% Ethanol, 2% citric acid, 2% malic acid, 1.25% hydroxyethylcellulose, and skin emollients This example illustrates that compositions of the present invention also provide a rapid and broad spectrum antibacterial activity.

Example 4

The following compositions were prepared to test the effect of organic acids and organic acid blends on skin pH and antiviral efficacy.

| Sample | Composition (by wt %) | Average Skin pH (T = 0) | Average Skin pH (T = 2 hr) |
|---|---|---|---|
| A | 4% citric acid in 70% ethanol/water | 2.97 | 3.64 |
| B | 4% malic acid in 70% ethanol/water | 2.91 | 3.94 |
| C | 2% citric acid and 2% malic acid in 70% ethanol/water | 2.99 | 3.38 |
| D | 4% tartaric acid in 70% ethanol/water | 2.56 | 3.0 |

The clean fingerpads of the test subjects were treated with Samples A-D. Baseline skin pH readings were measured from the fingerpads prior to treatment with a composition. Skin pH measurements also were taken immediately after the composition dried on the fingerpads, and again after two hours.

All Samples A-D suppressed skin pH to below 4 for two hours. The combination of citric acid and malic acid (Sample C) maintained a lower pH at two hours than the same acids used singly (Samples A and B). The 4% tartaric acid composition (Sample D) showed the greatest suppression of skin pH.

Example 5

The clean fingerpads of test subjects were treated with the following compositions. Baseline skin pH readings were measured from the fingerpads prior to treatment with the compositions. Skin pH measurements also were taken immediately after the composition dried on the fingerpads, then again after four hours.

| Sample | Composition (by wt %) | Average Skin pH (T = 0) | Average Skin pH (T = 4 hr) | Viral Log 10 Reduction | % Hands with Virus |
|---|---|---|---|---|---|
| A | 2% citric acid, 2% malic acid, 62% ETOH, 1.25% hydroxyethylcellulose | 2.81 | 3.23 | >3 log$_{10}$ | 0 |
| B | 2% citric acid, 2% tartaric acid, 62% ETOH, 1.25% hydroxyethylcellulose | 2.64 | 3.03 | >3 log$_{10}$ | 0 |
| C | 2% malic acid, 2% tartaric acid, 62% ETOH, 1.25% hydroxyethylcellulose | 2.66 | 2.94 | >3 log$_{10}$ | 0 |
| D | 62% ETOH, 1.25% hydroxyethylcellulose | 5.53 | 5.13 | <0.5 log$_{1-}$ | 100 |
| E | 2% citric acid, 2% malic acid, 70% ETOH, 1% polyacrylic acid | 2.90 | 3.72 | >3 log$_{10}$ | 0 |

| Sample | Composition (by wt %) | Average Skin pH (T = 0) | Average Skin pH (T = 4 hr) | Viral Log 10 Reduction | % Hands with Virus |
|---|---|---|---|---|---|
| F | 70% ETOH, 1% polyacrylic acid | 4.80 | 5.16 | 2.0 log$_{10}$ | 100 |
| G | 70% ETOH, 1.25% hydroxyethylcellulose | 5.3 | 5.25 | <0.5 log$_{10}$ | 100 |

[1]ETOH is ethanol

Four hours after treatment of the fingerpads with Samples A-G, Rhinovirus 39 at a titer of $1.3 \times 10^5$ pfu (plaque forming units) was applied to fingerpads. The virus was dried on the fingerpads for 10 minutes, then the fingerpads were rinsed with a viral recovery broth containing 75% EBSS and 25% FBS with 1× antibiotics. The sample was diluted serially in viral recovery broth and plated onto H1-HeLa cells. Titers were assayed as per the plaque assay. Complete inactivation of Rhinovirus 39, i.e., a greater than 3 log reduction, was achieved using the acid-containing compositions containing a mixture of two of citric acid, malic acid, and tartaric acid. The presence of hydroxyethylcellulose or polyacrylic acid assisted in forming a more continuous film or layer of organic acids on the treated fingerpads, which in turn enhanced the persistent antiviral activity of the compositions.

The following examples illustrate that polymeric acids, and especially an acrylic acid homopolymer or copolymer, in the presence of alcohol impart antiviral efficacy. The polymeric acids have a low pH and good substantivity to skin, which effectively maintains a low skin pH over time, and helps provide a persistent antiviral efficacy. The polymeric acids also help provide an essentially continuous layer or film of an organic acid on treated surfaces, which in turn enhances the persistent antiviral activity of the composition.

A synergistic effect on the lowering of skin pH was demonstrated with using acrylic acid-based polymer in the presence of alcohol. However, an acrylic acid-based polymer in the absence of an alcohol did not maintain a reduced skin pH to the same degree over time. Importantly, skin pH reduction is less dependent on composition pH when a polymeric acid is used in conjunction with an alcohol. The synergy demonstrated between the polymeric acid and the alcohol was unexpected and is a novel way of providing the lowered skin pH that provides a desired antiviral efficacy.

A synergistic effect on a rapid and persistent antiviral activity also is demonstrated when an acrylic acid-based polymer is used in conjunction with polycarboxylic acids. It has been found that utilizing a low amount of a polymeric acid (e.g., about 0.1% to about 2%, by weight) together with a polycarboxylic acid, like citric acid, malic acid, tartaric acid, and mixtures thereof, enhances the antiviral activities of the polycarboxylic acids. This synergistic effect allows a reduction in the polycarboxylic acid concentration in an antiviral composition, without a concomitant decrease in antiviral efficacy. This reduction in polycarboxylic acid concentration improves composition mildness by reducing the irritation potential of the composition. It is theorized, but not relied upon herein, that the polymeric acid assists in forming a residual barrier film or layer of organic acids on a treated surface, which enhance the persistent antiviral activity of the composition.

Example 6

A composition containing a polyacrylic acid (1% by wt), i.e., ULTREZ 20, available from Noveon Europe, was prepared in 70% aqueous ethanol and in water. Each composition (1.8 ml) was applied to the thumb, index, and middle fingers of a test subject. Skin pH readings were measured prior to treatment (baseline), immediately after the fingers were dry, and again after two hours. The average skin pH readings are summarized below.

| | Average skin pH | | |
|---|---|---|---|
| | Baseline | T = 0 | T = 2 hrs. |
| 70% ethanol | 5.65 | 5.3 | 5.2 |
| Polyacrylic acid (1%) (70% aqueous ethanol) | 5.63 | 4.4 | 4.5 |
| Polyacrylic acid (1%) (water) | 5.64 | 4.5 | 4.7 |

The polyacrylic acid suppressed skin pH to about 4.5 initially, and skin pH remains under 5 after two hours. The composition with ethanol suppressed skin pH slightly lower (4.4) than the composition free of ethanol (4.5). This result suggests a synergistic effect on lowering skin pH when a polyacrylic acid is applied with ethanol.

This data illustrates that polyacrylic acid suppresses skin pH resulting in antiviral efficacy. The data also illustrates that polyacrylic acid and ethanol act synergistically to lower skin pH, thus resulting in a greater efficacy against influenza viruses, including avian flu viruses.

To demonstrate this efficacy, the following eight compositions were prepared, wherein solutions containing a polyacrylic acid (with and without ethanol) were buffered to a pH of about 4.5, 5.0, 5.5, or 6.0.

| Sample | Composition (by wt %) | Solution pH | Avg. Skin Ph 2 hrs. |
|---|---|---|---|
| A | 1% ULTREZ 20/70% ethanol | 4.54 | 4.52 |
| B | 1% ULTREZ 20/70% ethanol | 5.10 | 4.87 |
| C | 1% ULTREZ 20/70% ethanol | 5.54 | 4.41 |
| D | 1% ULTREZ 20/70% ethanol | 6.17 | 4.32 |
| E | 1% ULTREZ 20 | 4.57 | 4.93 |
| F | 1% ULTREZ 20 | 5.12 | 5.46 |
| G | 1% ULTREZ 20 | 5.55 | 5.33 |
| H | 1% ULTREZ 20 | 6.32 | 5.70 |

The effect of the eight compositions on skin pH was tested. Each composition (1.8 ml) was applied to the thumb, index, and middle fingers of a test subject. Skin pH readings were measured prior to treatment (baseline), immediately after the product had dried, and again after two hours.

The skin pH data indicated that a polyacrylic acid and ethanol function synergistically to suppress skin pH because each composition containing ethanol in combination with the polyacrylic acid suppressed skin pH to a lower value than compositions free of ethanol. Compositions containing ethanol and polyacrylic acid lowered skin pH to between pH 4 and 5 independent of the solution pH. In contrast, compositions free of ethanol suppress the skin pH only to between pH 5-6 and the final skin pH is similar to the solution pH.

Example 7

The following compositions were prepared to further illustrate the antiviral efficacy provided by a polyacrylic acid.

| Sample | Composition (by wt %) Thickeners | Solution pH | Avg. Skin pH 2 hrs. |
|---|---|---|---|
| A | 1% polyacrylic acid | 4.21 | 4.7 |
| B | 5.5% CRODAFOS Acid[1] | 5.41 | 5.0 |
| C | 1.25% NATROSOL 250 HHR CS[2] | 6.32 | 5.3 |

[1] CRODAFOS CS20 Acid is Ceteth-20 & Cetaryl Alcohol & Dicetyl Phosphate; and
[2] NATROSOL 250 HHR CS is hydroxyethylcellulose.

Samples A-C (1.8 ml) were applied to the thumb, index, and middle fingers of clean hands. Skin pH readings were taken prior to treatment (baseline), immediately after the fingers were dry, and again after two hours for Samples A and B and after four hours for Sample C. The averages of the skin pH values are provided in the above table.

Sample A containing polyacrylic acid lowered the skin pH to the greatest extent with a final skin pH after two hours of pH 4.7. Neither Sample B nor Sample C lowered the skin pH below pH 5.0. This data indicates that polyacrylic acid has an ability to suppress skin pH and maintain a low skin pH for a least two hours.

Example 8

The use of a polyacrylic acid and ethanol in a composition suppresses skin pH to a value below the solution pH, as demonstrated in Example 8. To test whether antiviral compositions containing citric acid, malic acid, polyacrylic acid, and ethanol can be buffered to a higher solution pH and still provide a skin pH at or below pH 4 to obtain a persistent antiviral activity, the following compositions were prepared.

| Sample | Composition (by wt %) | Solution pH | Skin pH Initial | Skin pH 4 hrs. |
|---|---|---|---|---|
| A | 1% ULTREZ 20/2% citric acid/2% malic acid/70% ethanol | 3.2 | 2.9 | 3.7 |
| B | 1% ULTREZ 20/2% citric acid/2% malic acid/70% ethanol | 4.34 | 3.4 | 3.7 |
| C | 1% ULTREZ 20/2% citric acid/2% malic acid/70% ethanol | 4.65 | 3.6 | 3.8 |

The compositions (1.8 mL) were applied to the thumb, index, and middle fingers of clean hands. Skin pH readings were measured prior to treatment (baseline), immediately after the fingers were dry, and again after four hours. The average of the skin pH values are plotted above.

Initial skin pH of skin treated with Samples A-C were suppressed to between pH 2.9 and 3.6, wherein the lower the solution pH, the lower the initial skin pH. However, after four hours, the skin pH for all three compositions was about pH 3.7. Consistent with previous examples, solution pH did not predict subsequent skin pH.

This data demonstrates than when citric acid and malic acid are utilized in a composition in combination with a polyacrylic acid and ethanol, the pH of the solution can be buffered to a higher, e.g., milder and safer, pH for application to the skin, while still retaining an ability to suppress skin pH and exhibit antiviral activity. This result also is attributed, at least in part, to the residual layer or film of organic acid that remains on the skin after evaporation of volatile composition ingredients.

The following tests demonstrate that a composition of the present invention provides an essentially continuous barrier layer of organic acid on a treated surface. In particular, the following tests show that a present composition resists rinsing from a treated surface, e.g., at least 50% of the nonvolatile composition ingredients (including the organic acid) remains on a treated surface after three rinsings, as determined from NMR and IR spectra. In addition, an effective antiviral amount of the nonvolatile composition ingredients remains on a treated surface after 10 rinsings, also determined using NMR and IR spectra.

In the following tests, an aqueous composition containing, by weight, 2% malic acid, 2% citric acid, 1% polyacrylic acid, 62% ethanol, and 0.5% hydroxyethylcellulose as a gelling agent (Composition A) was compared to an aqueous composition, containing 2% malic acid, 2% citric acid, and 62% ethanol (Composition B). The compositions were applied to a glass surface to provide a film. From infrared (IR) and nuclear magnetic resonance (NMR) spectra of the film taken after each rinse, it was determined that Composition B was completely rinsed from the surface after one rinsing with water. Composition B therefore failed to exhibit water resistance and failed to provide a film or layer of nonvolatile composition ingredients on the surface.

In contrast, IR and NMR spectra showed that Composition A provided a rinse-resistant film or layer of composition ingredients on the treated surface. The amount of composition ingredients that remained on the treated surface was reduced over the first three rinsings, then resisted further removal from the treated surface in subsequent rinses. The IR and NMR spectra showed that detectable and effective amounts of the nonvolatile composition ingredients remained on the treated surface after 10 water rinses.

Another test was performed to measure the contact angle of water on a surface. "Contact angle" is a measure of the wetting ability of water on a surface. In this test, Compositions A and B were applied to a glass surface and allowed to dry. Contact angle then was measured for glass treated with Compositions A and B, both unrinsed and rinsed, using deionized water. The contact angle of bare, i.e., untreated, glass also was measured as a control. The following table summarizes the results of the contact angle test.

| | Composition A Unrinsed | Composition A Rinsed | Composition Unrinsed | Composition Rinsed | Bare Glass |
|---|---|---|---|---|---|
| Avg Reading (degrees) | 45.96 | 72.66 | 6.69 | 41.51 | 38.47 |
| Change in degrees | | 26.7 | | 34.8 | |
| % Change | | 58.1 | | 520.2 | |

The contact angle data shows that Composition A modifies the glass surface and provides a persistent barrier film or layer on the glass surface. The data also shows that Composition B is rinsed from the surface because the contact angle after rinsing of Composition B is essentially the same as that of bare glass.

Another test was performed to demonstrate metal ion uptake by a residual film of Composition A. In this test, films of Composition A were formed on glass, dried at least 4 hours, then exposed to solutions having a 0.5 M concentration of metal ions. Samples then were analyzed by SEM scan. The data in the following table shows that a film resulting from Composition A effectively binds several types of metal ions. It is theorized, but not relied upon, that this is a surface phenomenon because no mechanism for transporting metal ions into the film is known.

| Composition A Films on Glass (Metal-Soaked & Deionized Water Rinsed) (unless otherwise specified) | | |
| --- | --- | --- |
| Soaking Solution | EDS atomic % | EDS wt % |
| 0.56 wt % CaCl$_2$ in formula on 316 SS - No Rinse | 0.63% Ca | 1.71% Ca |
| 0.1 M Ca on 316 SS | 0.13% Ca | 0.21% Ca |
| 0.5 M Ca on 316 SS | 0.34% Ca | 0.54% Ca |
| 0.5 M Ca w/ more rinsing on 316 SS | 0.07% Ca | 0.12% Ca |
| 0.5 M Cu on 316 SS | 0.65% Cu | 1.59% Cu |
| 0.5 M Fe on Al 6061 | 0.41% Fe | 1.14% Fe |
| 0.5 M Zn on Al 6061 | 0.24% Zn | 0.90% Zn |
| Metal Coupon anzlysis | | |
| DI water on 316 SS Fe compensated for in above datum | 0% Ca, 0% Cu, 0% Zn | 0% Ca, 0% Cu, 0% Zn |
| DI water on Al 6061 | 0.07% Ca, 0.08% Fe, 0.03% Cu [from Al] | 0.18% Ca, 0.29% Fe, 0.11% Cu [from Al] |

Figure 1C:
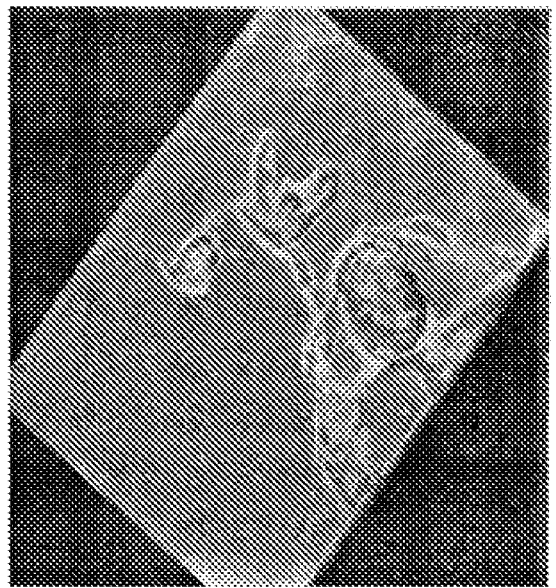
FIGS. 1*c* and 1*d* are reflectance micrographs showing the absence of a barrier layer on a surface after application of a control composition to the surface.
Figure 1B:
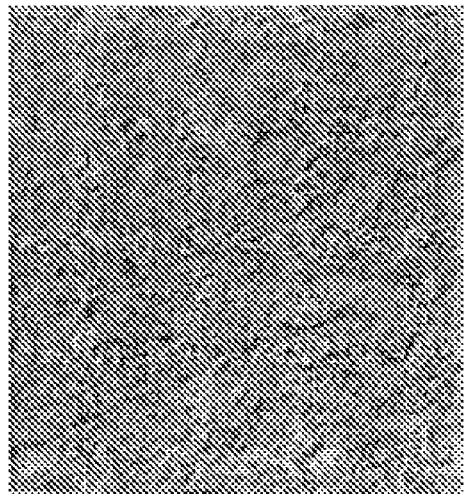
Figure 1D:
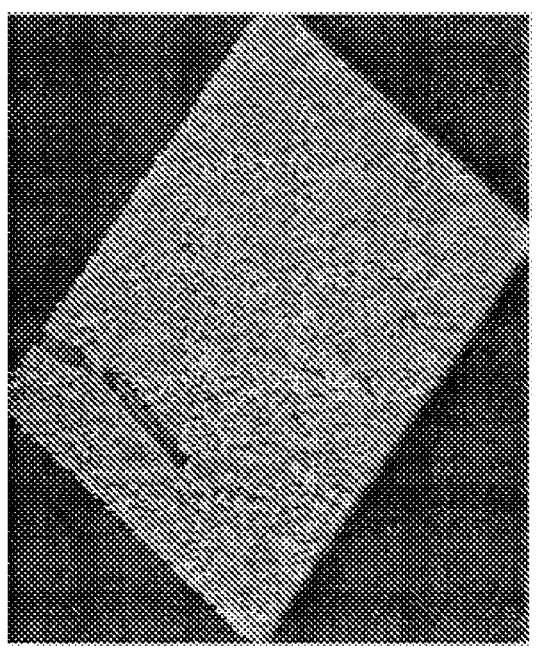

Reflectance micrographs showing the surface coverage of Compositions A and B also were taken (FIG. 1). The attached micrographs show that Composition A provides an essentially complete surface coverage, i.e., a more even coverage of Composition A on a treated surface, which provides an essentially continuous layer or film of nonvolatile composition ingredients on the surface. The attached micrographs are a digital conversion of reflectance values, which provide a direct correlation to surface coverage. The micrographs demonstrate that Composition A (FIGS. 1*a*) and 1*b*)) provides a film having improved adhesion, dispersion, and crystal formation compared to Composition B (FIGS. 1*c*) and 1*d*)).

A present composition capable of efficacy against influenza viruses can be formulated into a variety of product forms, including liquids, gels, semisolids, and solids. The liquid product form can be a solution, dispersion, emulsion, or a similar product form. The gel and semisolid product forms can be transparent or opaque, designed for application by stick dispenser or by the fingers, for example. The solid product forms can be a powder, flake, granule, tablet, pellet, lozenge, puck, briquette, brick, solid block, unit dose, or a similar solid product form known in the art. The present antimicrobial compositions can be manufactured as dilute ready-to-use compositions, or as concentrates that are diluted prior to use.

One particular product form is a liquid or solid composition disposed within a water-soluble packet. The packet is added to a proper amount of water, and the composition is released when the packet dissolves. The water-soluble packet typically comprises a polyvinylalcohol. One form of water-soluble packet is disclosed in U.S. Pat. No. 5,316,688, incorporated herein by reference. Numerous other water-soluble packets are known to person skilled in the art, for example, in U.S. Pat. Nos. 5,070,126; 6,608,121; and 6,787,512; U.S. Patent Publication No. 2002/0182348; WO 01/79417; and European Patent Nos. 0-444 230, 1 158 016, 1 180 536, and 1 251 147, each incorporated herein by reference. Capsules are another related and useful product form.

Another useful product form is a stable, solid block that can be added to water to provide a liquid composition for practicing the present methods. The block can be tablet, briquette, puck, or larger solid block, e.g., the block can weigh from less than one ounce to several pounds, depending on the end use application. Such blocks generally comprise a binding agent. One stable block is disclosed in U.S. Pat. No. 6,432,906, incorporated herein by reference.

Yet another product form is incorporation of the composition into an absorbent or adsorbent carrier, such as polymeric microparticles or inorganic particles. The loaded carrier can be used as is, or incorporated into other product forms, either liquid, gel, semisolid, or solid.

Still another product form is a web material or swab containing a present composition capable of controlling influenza virus. The composition then can be applied to the skin or an inanimate surface by wiping the surface with the web material containing the composition.

Another product form is an article, such as latex gloves, having the composition applied to, or imbedded into, the article. During use, the composition imparts antiviral activity to the article itself and/or to a surface contacted by the article. Additional articles that can have a present composition imbedded therein are plastic cups, food wraps, and plastic containers.

As discussed above, both animate and inanimate surfaces can be treated in accordance with the method of the present invention. A particularly important surface is mammalian skin, and especially human skin, to inactivate and interrupt the transmission of bacteria and viruses. However, the present method also is useful in treating other animate surfaces and inanimate surfaces of all types.

For example, a present composition can be applied to food products, such as meat, poultry, seafood, fruits, and vegetables. The compositions are applied to the surfaces of food products to control microorganisms. Examples of microorganisms include pathogenic microorganisms that can cause illness (e.g., *Listeria monocytogenes*, enterohemorrhagic *Escherichia coli, Salmonella*, and the like) and spoilage organisms that can affect the taste, color, and/or smell of the final food product (e.g., *Pseudomonas, Acinetobacter, Moraxella, Alcaligenes, Flavobacterium, Erwinia*, and the like).

The compositions can be applied to any food product that is consumed by a human or an animal, including both food and beverages, and specifically meat, poultry, seafood, fruits, and vegetables. Some nonlimiting examples of meat products include muscle meat or any portion thereof of any animal including beef, pork, veal, buffalo, and lamb. Some nonlimiting examples of seafood include scallops, shrimp, crab, octopus, mussels, squid, and lobsters. Some nonlimiting examples of poultry include chicken, turkey, ostrich, game hen, squab, guinea fowl, pheasant, duck, goose, and emu. Some nonlimiting examples of fruits and vegetables include citrus fruits, tree fruits, tropical fruits, berries, lettuce, green beans, peas, carrots, tomatoes, mushrooms, potatoes, root vegetables, sprouts, seeds, nuts, animal feed, and grains such as corn, wheat, and oats.

The compositions can be applied to the surface of the food product in several ways including spraying, misting, rolling, and foaming the composition onto the food product, or immersing the food product in the composition. The composition can be applied by injection, such as in an injection solution, or the composition can be applied as a component of a marinade or tenderizer that is applied to the food product. The application of the composition can be combined with physical agitation, such as spraying with pressure, rubbing, or brushing. Application of the composition can be manual, or the composition can be applied in a spray booth. The spray can comprise of fog material delivered from a fogging apparatus as a dispersion of fog particles in a continuous atmosphere. The composition can be used on a food product once, then discarded, or the composition can be recycled.

The food product also can be immersed into a container containing the composition. The composition preferably is agitated to increase the efficacy of this solution and the speed in which the solution kills microorganisms attached to the food product.

In another embodiment of the present invention, the food product can be treated with a foaming version of the composition. The foam can be prepared by mixing a foaming surfactant with the composition at the time of use. The foaming surfactants can be nonionic, anionic, or cationic in nature.

In still another embodiment of the invention, the food product can be treated with a thickened or gelled composition. In the thickened or gelled state, the compositions remain in contact with the food product for longer periods of time, thus increasing the antimicrobial efficacy. The thickened or gelled composition also adheres to vertical surfaces.

The volume of composition per pound of foodstuff is an important parameter with respect to the antimicrobial efficacy of the compositions. Preferred volumes of the composition for treated poultry, fish, fruits, and vegetables and red meat pieces/trim are about 0.5 oz/lb to about 3.0 oz/lb, and more preferably, about 1.0 to about 2.0 oz/lb of foodstuff in dip and spray applications. For beef carcasses, the preferred volumes are about 0.5 to about 2.5 gallons per side of beef, and more preferably about 1.0 to about 2.0 gallons/side.

The treatment of food products with a disinfecting composition is described in greater detail in U.S. Pat. Nos. 5,389,390; 5,409,713; 6,063,425; 6,183,807; 6,113,963; 6,514,556; and 6,545,047, the disclosures of which are incorporated by reference herein in their entirety.

The compositions also can be applied to live animals, for example, as teat dips or hoof treatments. Teat dips are known as a method of reducing bovine mastitis in dairy herds. Mastitis is one of the most common and economically costly diseases confronting milk producers. Economic losses result from poor milk quality, lower milk production, and potential culling of chronically infected animals. The use of an antimicrobial composition both before and after milking has found great success in preventing mastitis. When a composition is used as a teat dip, it may be desirable to add additional ingredients that enhance the effectiveness of the composition or provide additional benefit, such as a dye to indicate that the composition has been properly applied.

The composition also can be used as a foot bath or hoof treatment to prevent the spread of diseases. For example, the composition can be formulated and applied such that farm workers walk through the composition and thereby prevent microorganisms on their boots from spreading. Alternatively, the composition can be used in such a way that animals walk through the composition, thereby preventing the spread of microorganisms, and also providing an opportunity to treat any infections on the hooves of the animals.

The present method also is useful to treat inanimate surfaces, both soft and hard. As used herein, the term "hard" refers to surfaces comprising refractory materials, such as glazed and unglazed tile, brick, porcelain, ceramics, metals, glass, and the like, and also includes wood and hard plastics, such as formica, polystyrenes, vinyls, acrylics, polyesters, and the like. A hard surface can be porous or nonporous. Methods of disinfecting hard surfaces are described in greater detail in U.S. Pat. Nos. 5,200,189; 5,314,687; and 5,718,910, each disclosure incorporated herein by reference.

The present method can be used to treat hard surfaces in processing facilities (such as dairy, poultry, brewing, and food processing facilities), healthcare facilities (such as hospitals, clinics, surgical centers, dental offices, and laboratories), long-term healthcare facilities (such as nursing homes), farms, cruise ships, hotels, airplanes, schools, and private homes.

The present method can be used to treat environmental surfaces such as floors, walls, ceilings, and drains. The method can be used to treat equipment such as food processing equipment, dairy processing equipment, brewery equipment, and the like. The compositions can be used to treat a variety of surfaces including food contact surfaces in food, poultry, dairy, and brewing facilities, such as countertops, furniture, sinks, and the like. The method further can be used to treat tools and instruments, such as medical tools and instruments, dental tools and instruments, as well as equipment used in the healthcare industries and institutional kitchens, e.g., knives, forks, spoons, wares (such as pots, pans, and dishes), cutting equipment, and the like.

Treatable inanimate surfaces include, but are not limited to, exposed environmental surfaces, such as tables, floors, walls, kitchenware (including pots, pans, knives, forks, spoons, plates), food cooking and preparation surfaces, including dishes and food preparation equipment, tanks, vats, lines, pumps, hoses, and other process equipment. One useful application of the composition is to treat poultry processing equipment. Poultry process equipment can be found in poultry farm installations and in poultry plant installations for the processing of chickens, turkeys, and other poultry products. Another useful application is to treat surfaces contacted by raw poultry and food, such as in supermarkets, restaurants, butcher shops, kitchens, and similar installations.

In use, the compositions are applied to target animate and inanimate surfaces. The compositions can be applied by dipping a surface into the composition, soaking a surface in the composition, or spraying, wiping, foaming, misting, brushing, pod coating, rolling, and fogging the composition onto an animate or inanimate surface. The composition can be applied manually or using equipment such as a spray bottle or by machine, such as a spray machine, foam machine, and the like. The composition can also be used inside a machine, such as a warewashing machine or laundry machine. For household applications, hand-operated pump-type or pressurized aerosol sprayers can be used. The compositions also can be employed to coat or otherwise treat materials such as sponges, fibrous or nonfibrous web materials, swabs, flexible plastics, textiles, wood, and the like. Generally, the coating process is used to impart prolonged antiviral properties to a porous or nonporous surface by coating said surface with the composition.

The method of the present invention also can be used in the manufacture of beverages including fruit juice, malt beverages, bottled water products, teas, and soft drinks. The method can be used to treat pumps, lines, tanks, and mixing equipment used in the manufacture of such beverages. The method of the present invention also can be used to treat air filters.

The method of the present invention is useful in the treatment of medical carts, medical cages, and other medical instruments, devices, and equipment. Examples of medical apparatus treatable by the present method are disclosed in U.S. Pat. No. 6,632,291, incorporated herein by reference. The present method also is useful in treating utensil and chairs present in barber shops, and hair and nail salons. A further useful application is to treat coins, paper money, tokens, poker chips, and similar articles that are repeatedly handled by numerous individuals and can transmit viruses between individuals.

In addition to hard surfaces, the method also can be used to treat soft inanimate surfaces, like textiles, such as clothing, protective clothing, laboratory clothing, surgical clothing, patient clothing, carpets, bedding, towels, linens, and the like. The method also can be used to treat face masks, medical gowns, gloves, and related apparel utilized by medical and dental personnel.

The antimicrobial compositions of the present invention have several practical end uses, including surgical scrubs, body splashes, antiseptics, disinfectants, hand sanitizer gels, deodorants, and similar personal care products. Additional types of compositions include foamed compositions, such as creams, mousses, and the like, and compositions containing organic and inorganic filler materials, such as emulsions, lotions, creams, pastes, ointments, and the like. The compositions further can be used as an antimicrobial for hard surfaces, for example, sinks and countertops in hospitals, food service areas, cruise ships, nursing homes, schools, and meat and poultry processing plants. The present antimicrobial compositions can be manufactured as dilute ready-to-use compositions, or as concentrates that are diluted prior to use.

The present invention, therefore, encompasses applying an effective amount of an antimicrobial compositions of the present invention onto nonskin surfaces, such as household surfaces, e.g., countertops, kitchen surfaces, food preparing surfaces (cutting boards, dishes, pots and pans, and the like); major household appliances, e.g., refrigerators, freezers, washing machines, automatic dryers, ovens, microwave ovens, and dishwashers; cabinets; walls; floors; bathroom surfaces, shower curtains, garbage cans, and/or recycling bins, and the like.

The compositions also can be incorporated into a web material to provide an antimicrobial wiping article. The wiping article can be used to clean and sanitize animate or inanimate surfaces. The compositions also can be incorporated into a swab.

In one embodiment of the present invention, a person who either (a) is exposed, or likely to be exposed, to an influenza virus, and particularly an avian flu virus, or is likely to be exposed to other individuals exposed to an influenza virus, or (b) is likely to be exposed to other individuals suffering from an influenza virus infection, can apply a present antimicrobial composition to his or her hands. This application kills bacteria and inactivates influenza virus particles present on the hands. The applied composition, either rinsed off or allowed to remain on the hands, provides a persistent antiviral activity. Avian flu viruses, like H5 viruses, therefore, cannot be transmitted to noninfected individuals via hand-to-hand or bird-to-hand transmission. The amount of the composition applied, the frequency of application, and the period of use will vary depending upon the level of disinfection desired, e.g., the degree of microbial contamination and/or skin soiling.

The present antimicrobial compositions provide the advantages of a broad spectrum kill of Gram positive and Gram negative bacteria, and an influenza virus control, in short contact times. The short contact time for a substantial log reduction of bacteria is important in view of the typical 15 to 60 second time frame used to sanitize the skin and inanimate surfaces. The composition also imparts a persistent antiviral activity to the contacted surface. The present compositions are effective in short contact time because of the synergistic effect provided by the combination of a disinfecting alcohol and an organic acid and a persistent activity is enhanced because of a residual barrier layer or film of composition ingredients that can remain on the skin after evaporation of the volatile components of the composition.

Obviously, many modifications and variations of the invention as hereinbefore set forth can be made without departing from the spirit and scope thereof, and, therefore, only such limitations should be imposed as are indicated by the appended claims.

What is claimed is:

1. A method of reducing an avian flu virus population on a surface comprising contacting the surface with a composition for 30 seconds to achieve a log reduction of at least 1.5 against the avian flu virus, said composition comprising:
   (a) about 25% to about 75%, by weight of a disinfecting alcohol;
   (b) a virucidally effective amount of an organic acid comprising (i) a polycarboxylic acid comprising citric acid and malic acid and (ii) a polymeric carboxylic acid comprising a homopolymer or a crosspolymer of acrylic acid;
   (c) about 0.1% to about 3%, by weight, of a gelling agent selected from the group consisting of cellulose, a cellulose derivative, guar, a guar derivative, algin, an algin derivative, carrageenan, and mixtures thereof, and
   (d) water,
   wherein the composition has a pH of about 5 or less at 25° C., and is free of an active antimicrobial agent selected from the group consisting of a phenolic antimicrobial agent, a quaternary ammonium antimicrobial agent, an anilide antimicrobial agent, and a bisguanidine antimicrobial agent, and wherein an essentially continuous layer comprising the organic acid is formed on the surface.

2. The method of claim 1 wherein the avian flu virus comprises an H1, H2, H3, H4, H5, H6, H7, H8, H9, H10, H11, H12, H13, H14, H15, H16, N1, N2, N3, N4, N5, N6, N7, N8, or N9 subtype.

3. The method of claim 2 wherein the avian flu virus comprises an H5 subtype.

4. The method of claim 3 wherein the avian flu virus comprises H5N1 strain.

5. The method of claim 1 further comprising a step of rinsing the composition from the surface.

6. The method of claim 1 wherein the composition is allowed to remain on the surface and dry.

7. The method of claim 1 wherein the surface is a skin of a mammal.

8. The method of claim 7 wherein the composition lowers a pH of the skin to less than 4 after drying on the skin.

9. The method of claim 1 wherein the composition imparts a persistent activity against an avian flu virus.

10. The method of claim 1 wherein the disinfecting alcohol is present in the composition in an amount of about 30% to about 75%, by weight of the composition.

11. The method of claim 1 wherein the disinfecting alcohol comprises one or more $C_{1-6}$ alcohol.

12. The method of claim 1 wherein the disinfecting alcohol is selected from the group consisting of methanol, ethanol, isopropyl alcohol, n-butanol, n-propyl alcohol, and mixtures thereof.

13. The method of claim 1 wherein the composition comprises about 0.05% to about 15%, by weight, of an organic acid.

14. The method of claim 1 wherein the polymeric carboxylic acid has a molecular weight of about 500 to about 10,000,000 g/mol.

15. The method of claim 14 wherein the polymeric carboxylic acid is water soluble or water dispersible.

16. The method of claim 1 wherein the composition has a pH of about 2 to less than about 5.

17. The method of claim 8 wherein the skin of the mammal has a skin pH of less than 4 four hours after contact.

18. The method of claim 1 wherein the composition further comprises about 0.1% to about 30% of a polyhydric solvent selected from the group consisting of a diol, a triol, and mixtures thereof.

19. The method of claim 1 wherein the composition further comprises about 0.1% to about 30%, by weight, of a hydrotrope.

20. The method of claim 1 wherein the composition further comprises an anionic, a cationic, a nonionic, or an ampholytic surfactant.

21. The method of claim 1 wherein the composition imparts a log reduction of at least 1.5 against an avian flu virus at least about four hours after contact.

22. The method of claim 1 wherein the composition imparts a log reduction of at least 1.25 against an avian flu virus about six hours after contact.

23. The method of claim 1 wherein an effective amount of the organic acid remains in the barrier layer on the surface after ten rinsings with water.

24. The method of claim 1 wherein at least 50%, by weight, of the nonvolatile components of the composition are present on the surface after three rinses with water.

25. A method of inactivating an avian flu virus comprising topically applying a composition to a surface in need of such treatment,
   said composition comprising;
   (a) about 25% to about 75%, by weight of a disinfecting alcohol;
   (b) a virucidally effective amount of an organic acid comprising (i) a polycarboxylic acid comprising citric acid and malic acid and (ii) a polymeric carboxylic acid comprising a homopolymer or a crosspolymer of acrylic acid;
   (c) about 0.1% to about 3%, by weight, of a gelling agent selected from the group consisting of cellulose, a cellulose derivative, guar, a guar derivative, algin, an algin derivative, carrageenan, and mixtures thereof, and
   (d) water,
   wherein the composition has a pH of about 5 or less at 25° C., and is free of an active antimicrobial agent selected from the group consisting of a phenolic antimicrobial agent, a quaternary ammonium antimicrobial agent, an anilide antimicrobial agent, and a bisguanidine antimicrobial agent, and wherein an essentially continuous layer comprising the organic acid is formed on the surface.

26. The method of claim 25 wherein a persistent antiviral efficacy is imparted to the surface.

27. The method of claim 25 wherein the surface is animate.

28. The method of claim 25 wherein H5 viruses are inactivated.

29. The method of claim 25 wherein H5N1 virus is inactivated.

30. A method of protecting an individual against infection by avian flu viruses comprising applying a composition to hands of the individual in an amount sufficient to eradicate avian flu viruses,
   said composition comprising:
   (a) about 25% to about 75%, by weight, of a disinfecting alcohol;
   (b) a virucidally effective amount of an organic acid comprising (i) a polycarboxylic acid comprising citric acid and malic acid and (ii) a polymeric carboxylic acid comprising a homopolymer or a crosspolymer of acrylic acid;
   (c) about 0.1% to about 3%, by weight, of a gelling agent selected from the group consisting of cellulose, a cellulose derivative, guar, a guar derivative, algin, an algin derivative, carrageenan, and mixtures thereof, and
   (d) water,
   wherein the composition has a pH of about 5 or less at 25° C., and is free of an active antimicrobial agent selected from the group consisting of a phenolic antimicrobial agent, a quaternary ammonium antimicrobial agent, an anilide antimicrobial agent, and a bisguanidine antimicrobial agent, and wherein an essentially continuous layer comprising the organic acid is formed on the surface.

31. The method of claim 30 wherein the composition is applied prior to the individual being exposed to the avian flu virus.

32. The method of claim 30 wherein the composition is applied multiple times within a twenty-four hour period.

33. The method of claim 30 wherein the composition is rinsed from the hands.

34. The method of claim 30 wherein the composition is allowed to remain on the hands and dry.

* * * * *